United States Patent
Coakley

(10) Patent No.: US 7,796,403 B2
(45) Date of Patent: Sep. 14, 2010

(54) MEANS FOR MECHANICAL REGISTRATION AND MECHANICAL-ELECTRICAL COUPLING OF A FARADAY SHIELD TO A PHOTODETECTOR AND AN ELECTRICAL CIRCUIT

(75) Inventor: Joseph Coakley, Dublin, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 1021 days.

(21) Appl. No.: 11/529,021

(22) Filed: Sep. 28, 2006

(65) Prior Publication Data

US 2008/0117616 A1 May 22, 2008

(51) Int. Cl.
*H05K 9/00* (2006.01)
(52) U.S. Cl. .................. 361/816; 361/800; 361/818; 361/753; 361/799
(58) Field of Classification Search .......... 361/753, 361/799, 800, 816, 818; 174/350, 377; 600/344
See application file for complete search history.

(56) References Cited

U.S. PATENT DOCUMENTS

| | | | |
|---|---|---|---|
| 3,403,555 A | 10/1968 | Versaci et al. |
| 3,536,545 A | 10/1970 | Traynor et al. |
| D222,454 S | 10/1971 | Beeber |
| 3,721,813 A | 3/1973 | Condon et al. |
| 4,098,772 A | 7/1978 | Bonk et al. |
| D250,275 S | 11/1978 | Bond |
| D251,387 S | 3/1979 | Ramsay et al. |
| D262,488 S | 12/1981 | Rossman et al. |
| 4,334,544 A | 6/1982 | Hill et al. |
| 4,350,165 A | 9/1982 | Striese |
| 4,353,372 A | 10/1982 | Ayer |
| 4,380,240 A | 4/1983 | Jobsis et al. |
| 4,406,289 A | 9/1983 | Wesseling et al. |
| 4,510,551 A | 4/1985 | Brainard, II |
| 4,586,513 A | 5/1986 | Hamaguri |
| 4,603,700 A | 8/1986 | Nichols et al. |
| 4,621,643 A | 11/1986 | New, Jr. et al. |
| 4,653,498 A | 3/1987 | New, Jr. et al. |
| 4,677,528 A | 6/1987 | Miniet |
| 4,685,464 A | 8/1987 | Goldberger et al. |

(Continued)

FOREIGN PATENT DOCUMENTS

AU 2120892 4/1993

(Continued)

OTHER PUBLICATIONS

U.S. Appl. No. 11/519,714, filed Sep. 12, 2006, Raridan, Jr.

(Continued)

*Primary Examiner*—Dameon E Levi
(74) *Attorney, Agent, or Firm*—Fletcher Yoder

(57) ABSTRACT

A spectrophotometric sensor is provided that includes a mating surface upon which electrical and optical components may be secured and a Faraday shield assembly secured to the mating surface enclosing a photodetector. The Faraday shield assembly includes alignment features that may be employed to provide mechanical registration and/or electrical coupling of the Faraday shield assembly. The spectrophotometric sensor may be placed on a patient's finger, toe, ear, and so forth to obtain hemoglobin oxygen saturation using pulse oximetry, or for other physiological measurements.

21 Claims, 4 Drawing Sheets

U.S. PATENT DOCUMENTS

| | | | |
|---|---|---|---|
| 4,694,833 A | 9/1987 | Hamaguri |
| 4,697,593 A | 10/1987 | Evans et al. |
| 4,700,708 A | 10/1987 | New, Jr. et al. |
| 4,714,080 A | 12/1987 | Edgar, Jr. et al. |
| 4,714,341 A | 12/1987 | Hamaguri et al. |
| 4,722,120 A | 2/1988 | Lu |
| 4,726,382 A | 2/1988 | Boehmer et al. |
| 4,759,369 A | 7/1988 | Taylor |
| 4,770,179 A | 9/1988 | New, Jr. et al. |
| 4,773,422 A | 9/1988 | Isaacson et al. |
| 4,776,339 A | 10/1988 | Schreiber |
| 4,781,195 A | 11/1988 | Martin |
| 4,783,815 A | 11/1988 | Buttner |
| 4,796,636 A | 1/1989 | Branstetter et al. |
| 4,800,495 A | 1/1989 | Smith |
| 4,800,885 A | 1/1989 | Johnson |
| 4,802,486 A | 2/1989 | Goodman et al. |
| 4,805,623 A | 2/1989 | Jöbsis |
| 4,807,630 A | 2/1989 | Malinouskas |
| 4,807,631 A | 2/1989 | Hersh et al. |
| 4,819,646 A | 4/1989 | Cheung et al. |
| 4,819,752 A | 4/1989 | Zelin |
| 4,824,242 A | 4/1989 | Frick et al. |
| 4,825,872 A | 5/1989 | Tan et al. |
| 4,825,879 A | 5/1989 | Tan et al. |
| 4,830,014 A | 5/1989 | Goodman et al. |
| 4,832,484 A | 5/1989 | Aoyagi et al. |
| 4,846,183 A | 7/1989 | Martin |
| 4,848,901 A | 7/1989 | Hood, Jr. |
| 4,854,699 A | 8/1989 | Edgar, Jr. |
| 4,859,056 A | 8/1989 | Prosser et al. |
| 4,859,057 A | 8/1989 | Taylor et al. |
| 4,863,265 A | 9/1989 | Flower et al. |
| 4,865,038 A | 9/1989 | Rich et al. |
| 4,867,557 A | 9/1989 | Takatani et al. |
| 4,869,253 A | 9/1989 | Craig, Jr. et al. |
| 4,869,254 A | 9/1989 | Stone et al. |
| 4,880,304 A | 11/1989 | Jaeb et al. |
| 4,883,055 A | 11/1989 | Merrick |
| 4,883,353 A | 11/1989 | Hansman et al. |
| 4,890,619 A | 1/1990 | Hatschek |
| 4,892,101 A | 1/1990 | Cheung et al. |
| 4,901,238 A | 2/1990 | Suzuki et al. |
| 4,908,762 A | 3/1990 | Suzuki et al. |
| 4,911,167 A | 3/1990 | Corenman et al. |
| 4,913,150 A | 4/1990 | Cheung et al. |
| 4,926,867 A | 5/1990 | Kanda et al. |
| 4,927,264 A | 5/1990 | Shiga et al. |
| 4,928,692 A | 5/1990 | Goodman et al. |
| 4,934,372 A | 6/1990 | Corenman et al. |
| 4,938,218 A | 7/1990 | Goodman et al. |
| 4,942,877 A | 7/1990 | Sakai et al. |
| 4,948,248 A | 8/1990 | Lehman |
| 4,955,379 A | 9/1990 | Hall |
| 4,960,126 A | 10/1990 | Conlon et al. |
| 4,964,408 A | 10/1990 | Hink et al. |
| 4,971,062 A | 11/1990 | Hasebe et al. |
| 4,974,591 A | 12/1990 | Awazu et al. |
| 5,007,423 A | 4/1991 | Branstetter et al. |
| 5,025,791 A | 6/1991 | Niwa |
| RE33,643 E | 7/1991 | Isaacson et al. |
| 5,028,787 A | 7/1991 | Rosenthal et al. |
| 5,035,243 A | 7/1991 | Muz |
| 5,040,539 A | 8/1991 | Schmitt et al. |
| 5,041,187 A | 8/1991 | Hink et al. |
| 5,054,488 A | 10/1991 | Muz |
| 5,055,671 A | 10/1991 | Jones |
| 5,058,588 A | 10/1991 | Kaestle |
| 5,065,749 A | 11/1991 | Hasebe et al. |
| 5,066,859 A | 11/1991 | Karkar et al. |
| 5,069,213 A | 12/1991 | Polczynski |
| 5,078,136 A | 1/1992 | Stone et al. |
| 5,086,229 A | 2/1992 | Rosenthal et al. |
| 5,088,493 A | 2/1992 | Giannini et al. |
| 5,090,410 A | 2/1992 | Saper et al. |
| 5,094,239 A | 3/1992 | Jaeb et al. |
| 5,094,240 A | 3/1992 | Muz |
| 5,099,841 A | 3/1992 | Heinonen et al. |
| 5,099,842 A | 3/1992 | Mannheimer et al. |
| H1039 H | 4/1992 | Tripp et al. |
| 5,104,623 A | 4/1992 | Miller |
| 5,109,849 A | 5/1992 | Goodman et al. |
| 5,111,817 A | 5/1992 | Clark et al. |
| 5,113,861 A | 5/1992 | Rother |
| D326,715 S | 6/1992 | Schmidt |
| 5,125,403 A | 6/1992 | Culp |
| 5,127,406 A | 7/1992 | Yamaguchi |
| 5,131,391 A | 7/1992 | Sakai et al. |
| 5,140,989 A | 8/1992 | Lewis et al. |
| 5,152,296 A | 10/1992 | Simons |
| 5,154,175 A | 10/1992 | Gunther |
| 5,158,082 A | 10/1992 | Jones |
| 5,170,786 A | 12/1992 | Thomas et al. |
| 5,188,108 A | 2/1993 | Secker et al. |
| 5,190,038 A | 3/1993 | Polson et al. |
| 5,193,542 A | 3/1993 | Missanelli et al. |
| 5,193,543 A | 3/1993 | Yelderman |
| 5,203,329 A | 4/1993 | Takatani et al. |
| 5,209,230 A | 5/1993 | Swedlow et al. |
| 5,213,099 A | 5/1993 | Tripp et al. |
| 5,216,598 A | 6/1993 | Branstetter et al. |
| 5,217,012 A | 6/1993 | Young et al. |
| 5,217,013 A | 6/1993 | Lewis et al. |
| 5,218,207 A | 6/1993 | Rosenthal |
| 5,218,962 A | 6/1993 | Mannheimer et al. |
| 5,224,478 A | 7/1993 | Sakai et al. |
| 5,226,417 A | 7/1993 | Swedlow et al. |
| 5,228,440 A | 7/1993 | Chung et al. |
| 5,237,994 A | 8/1993 | Goldberger |
| 5,239,185 A | 8/1993 | Ito et al. |
| 5,246,002 A | 9/1993 | Prosser |
| 5,246,003 A | 9/1993 | DeLonzor |
| 5,247,931 A | 9/1993 | Norwood |
| 5,247,932 A | 9/1993 | Chung et al. |
| 5,249,576 A | 10/1993 | Goldberger et al. |
| 5,253,645 A | 10/1993 | Friedman et al. |
| 5,253,646 A | 10/1993 | Delpy et al. |
| 5,259,381 A | 11/1993 | Cheung et al. |
| 5,259,761 A | 11/1993 | Schnettler et al. |
| 5,263,244 A | 11/1993 | Centa et al. |
| 5,267,562 A | 12/1993 | Ukawa et al. |
| 5,267,563 A | 12/1993 | Swedlow et al. |
| 5,267,566 A | 12/1993 | Choucair et al. |
| 5,273,036 A | 12/1993 | Kronberg et al. |
| 5,275,159 A | 1/1994 | Griebel |
| 5,278,627 A | 1/1994 | Aoyagi et al. |
| 5,279,295 A | 1/1994 | Martens et al. |
| 5,285,783 A | 2/1994 | Secker |
| 5,285,784 A | 2/1994 | Seeker |
| 5,287,853 A | 2/1994 | Vester et al. |
| 5,291,884 A | 3/1994 | Heinemann et al. |
| 5,297,548 A | 3/1994 | Pologe |
| 5,299,120 A | 3/1994 | Kaestle |
| 5,299,570 A | 4/1994 | Hatschek |
| 5,309,908 A | 5/1994 | Friedman et al. |
| 5,311,865 A | 5/1994 | Mayeux |
| 5,313,940 A | 5/1994 | Fuse et al. |
| 5,323,776 A | 6/1994 | Blakeley et al. |
| 5,329,922 A | 7/1994 | Atlee, III |
| 5,337,744 A | 8/1994 | Branigan |
| 5,339,810 A | 8/1994 | Ivers et al. |
| 5,343,818 A | 9/1994 | McCarthy et al. |
| 5,343,869 A | 9/1994 | Pross et al. |
| 5,348,003 A | 9/1994 | Caro |

| | | | | | |
|---|---|---|---|---|---|
| 5,348,004 A | 9/1994 | Hollub et al. | 5,575,284 A | 11/1996 | Athan et al. |
| 5,349,519 A | 9/1994 | Kaestle | 5,575,285 A | 11/1996 | Takanashi et al. |
| 5,349,952 A | 9/1994 | McCarthy et al. | 5,577,500 A | 11/1996 | Potratz |
| 5,349,953 A | 9/1994 | McCarthy et al. | 5,582,169 A | 12/1996 | Oda et al. |
| 5,351,685 A | 10/1994 | Potratz | 5,584,296 A | 12/1996 | Cui et al. |
| 5,353,799 A | 10/1994 | Chance | 5,588,425 A | 12/1996 | Sackner et al. |
| 5,355,880 A | 10/1994 | Thomas et al. | 5,588,427 A | 12/1996 | Tien |
| 5,355,882 A | 10/1994 | Ukawa et al. | 5,590,652 A | 1/1997 | Inai |
| 5,361,758 A | 11/1994 | Hall et al. | 5,595,176 A | 1/1997 | Yamaura |
| 5,365,066 A | 11/1994 | Krueger, Jr. et al. | 5,596,986 A | 1/1997 | Goldfarb |
| 5,368,025 A | 11/1994 | Young et al. | 5,611,337 A | 3/1997 | Bukta |
| 5,368,026 A | 11/1994 | Swedlow et al. | 5,617,852 A | 4/1997 | MacGregor |
| 5,368,224 A | 11/1994 | Richardson et al. | 5,626,140 A | 5/1997 | Feldman et al. |
| 5,372,136 A | 12/1994 | Steuer et al. | 5,629,992 A | 5/1997 | Amersfoort et al. |
| 5,377,675 A | 1/1995 | Ruskewicz et al. | 5,630,413 A | 5/1997 | Thomas et al. |
| 5,384,471 A * | 1/1995 | Schairer et al. ............... 257/98 | 5,632,272 A | 5/1997 | Diab et al. |
| 5,385,143 A | 1/1995 | Aoyagi | 5,632,273 A | 5/1997 | Suzuki |
| 5,387,122 A | 2/1995 | Goldberger et al. | 5,634,459 A | 6/1997 | Gardosi |
| 5,390,670 A | 2/1995 | Centa et al. | 5,638,593 A | 6/1997 | Gerhardt et al. |
| 5,392,777 A | 2/1995 | Swedlow et al. | 5,638,816 A | 6/1997 | Kiani-Azarbayjany et al. |
| 5,398,680 A | 3/1995 | Polson et al. | 5,638,818 A | 6/1997 | Diab et al. |
| 5,402,777 A * | 4/1995 | Warring et al. ............. 604/307 | 5,645,060 A | 7/1997 | Yorkey et al. |
| 5,402,779 A | 4/1995 | Chen et al. | 5,645,440 A | 7/1997 | Tobler et al. |
| 5,411,023 A | 5/1995 | Morris, Sr. et al. | 5,660,567 A | 8/1997 | Nierlich et al. |
| 5,411,024 A | 5/1995 | Thomas et al. | 5,662,105 A | 9/1997 | Tien |
| 5,413,099 A | 5/1995 | Schmidt et al. | 5,662,106 A | 9/1997 | Swedlow et al. |
| 5,413,100 A | 5/1995 | Barthelemy et al. | 5,664,270 A | 9/1997 | Bell et al. |
| 5,413,101 A | 5/1995 | Sugiura | 5,666,952 A | 9/1997 | Fuse et al. |
| 5,413,102 A | 5/1995 | Schmidt et al. | 5,671,529 A | 9/1997 | Nelson |
| 5,417,207 A | 5/1995 | Young et al. | 5,673,692 A | 10/1997 | Schulze et al. |
| 5,421,329 A | 6/1995 | Casciani et al. | 5,673,693 A | 10/1997 | Solenberger |
| 5,425,360 A | 6/1995 | Nelson | 5,676,139 A | 10/1997 | Goldberger et al. |
| 5,425,362 A | 6/1995 | Siker et al. | 5,676,141 A | 10/1997 | Hollub |
| 5,427,093 A | 6/1995 | Ogawa et al. | 5,678,544 A | 10/1997 | DeLonzor et al. |
| 5,429,128 A | 7/1995 | Cadell et al. | 5,680,857 A | 10/1997 | Pelikan et al. |
| 5,429,129 A | 7/1995 | Lovejoy et al. | 5,685,299 A | 11/1997 | Diab et al. |
| 5,431,159 A | 7/1995 | Baker et al. | 5,685,301 A | 11/1997 | Klomhaus |
| 5,431,170 A | 7/1995 | Mathews | 5,687,719 A | 11/1997 | Sato et al. |
| 5,437,275 A | 8/1995 | Amundsen et al. | 5,687,722 A | 11/1997 | Tien et al. |
| 5,438,986 A | 8/1995 | Disch et al. | 5,692,503 A | 12/1997 | Kuenstner |
| 5,448,991 A | 9/1995 | Polson et al. | 5,692,505 A | 12/1997 | Fouts |
| 5,452,717 A | 9/1995 | Branigan et al. | 5,709,205 A | 1/1998 | Bukta |
| 5,465,714 A | 11/1995 | Scheuing | 5,713,355 A | 2/1998 | Richardson et al. |
| 5,469,845 A | 11/1995 | DeLonzor et al. | 5,724,967 A | 3/1998 | Venkatachalam |
| 5,482,034 A | 1/1996 | Lewis et al. | 5,727,547 A | 3/1998 | Levinson et al. |
| 5,482,036 A | 1/1996 | Diab et al. | 5,730,124 A | 3/1998 | Yamauchi |
| 5,485,847 A | 1/1996 | Baker, Jr. | 5,731,582 A | 3/1998 | West |
| 5,490,505 A | 2/1996 | Diab et al. | D393,830 S | 4/1998 | Tobler et al. |
| 5,490,523 A | 2/1996 | Isaacson et al. | 5,743,260 A | 4/1998 | Chung et al. |
| 5,491,299 A | 2/1996 | Naylor et al. | 5,743,262 A | 4/1998 | Lepper, Jr. et al. |
| 5,494,032 A | 2/1996 | Robinson et al. | 5,743,263 A | 4/1998 | Baker, Jr. |
| 5,494,043 A | 2/1996 | O'Sullivan et al. | 5,746,206 A | 5/1998 | Mannheimer |
| 5,497,771 A | 3/1996 | Rosenheimer | 5,746,697 A | 5/1998 | Swedlow et al. |
| 5,499,627 A | 3/1996 | Steuer et al. | 5,752,914 A | 5/1998 | DeLonzor et al. |
| 5,503,148 A | 4/1996 | Pologe et al. | 5,755,226 A | 5/1998 | Carim et al. |
| 5,505,199 A | 4/1996 | Kim | 5,758,644 A | 6/1998 | Diab et al. |
| 5,507,286 A | 4/1996 | Solenberger | 5,760,910 A | 6/1998 | Lepper, Jr. et al. |
| 5,511,546 A | 4/1996 | Hon | 5,766,125 A | 6/1998 | Aoyagi et al. |
| 5,517,988 A | 5/1996 | Gerhard | 5,766,127 A | 6/1998 | Pologe et al. |
| 5,520,177 A | 5/1996 | Ogawa et al. | 5,769,785 A | 6/1998 | Diab et al. |
| 5,521,851 A | 5/1996 | Wei et al. | 5,772,587 A | 6/1998 | Gratton et al. |
| 5,522,388 A | 6/1996 | Ishikawa et al. | 5,774,213 A | 6/1998 | Trebino et al. |
| 5,524,617 A | 6/1996 | Mannheimer | 5,776,058 A | 7/1998 | Levinson et al. |
| 5,529,064 A | 6/1996 | Rall et al. | 5,776,059 A | 7/1998 | Kaestle |
| 5,533,507 A | 7/1996 | Potratz et al. | 5,779,630 A | 7/1998 | Fein et al. |
| 5,551,423 A | 9/1996 | Sugiura | 5,779,631 A | 7/1998 | Chance |
| 5,551,424 A | 9/1996 | Morrison et al. | 5,782,237 A | 7/1998 | Casciani et al. |
| 5,553,614 A | 9/1996 | Chance | 5,782,756 A | 7/1998 | Mannheimer |
| 5,553,615 A | 9/1996 | Carim et al. | 5,782,757 A | 7/1998 | Diab et al. |
| 5,555,882 A | 9/1996 | Richardson et al. | 5,782,758 A | 7/1998 | Ausec et al. |
| 5,558,096 A | 9/1996 | Palatnik | 5,786,592 A | 7/1998 | Hök |
| 5,560,355 A | 10/1996 | Merchant et al. | 5,788,634 A | 8/1998 | Suda et al. |
| 5,564,417 A | 10/1996 | Chance | 5,790,729 A | 8/1998 | Pologe et al. |

| | | | | | |
|---|---|---|---|---|---|
| 5,792,052 A | 8/1998 | Isaacson et al. | 5,987,343 A | 11/1999 | Kinast |
| 5,795,292 A | 8/1998 | Lewis et al. | 5,995,859 A | 11/1999 | Takahashi |
| 5,797,841 A | 8/1998 | DeLonzor et al. | 5,997,343 A | 12/1999 | Mills et al. |
| 5,800,348 A | 9/1998 | Kaestle | 5,999,834 A | 12/1999 | Wang et al. |
| 5,800,349 A | 9/1998 | Isaacson et al. | 6,002,952 A | 12/1999 | Diab et al. |
| 5,803,910 A | 9/1998 | Potratz | 6,005,658 A | 12/1999 | Kaluza et al. |
| 5,807,246 A | 9/1998 | Sakaguchi et al. | 6,006,120 A | 12/1999 | Levin |
| 5,807,247 A | 9/1998 | Merchant et al. | 6,011,985 A | 1/2000 | Athan et al. |
| 5,807,248 A | 9/1998 | Mills | 6,011,986 A | 1/2000 | Diab et al. |
| 5,810,723 A | 9/1998 | Aldrich | 6,014,576 A | 1/2000 | Raley et al. |
| 5,810,724 A | 9/1998 | Gronvall | 6,018,673 A | 1/2000 | Chin et al. |
| 5,813,980 A | 9/1998 | Levinson et al. | 6,018,674 A | 1/2000 | Aronow |
| 5,817,008 A | 10/1998 | Rafert et al. | 6,022,321 A | 2/2000 | Amano et al. |
| 5,817,009 A | 10/1998 | Rosenheimer et al. | 6,023,541 A | 2/2000 | Merchant et al. |
| 5,817,010 A | 10/1998 | Hibl | 6,026,312 A | 2/2000 | Shemwell et al. |
| 5,818,985 A | 10/1998 | Merchant et al. | 6,026,314 A | 2/2000 | Amerov et al. |
| 5,820,550 A | 10/1998 | Polson et al. | 6,031,603 A | 2/2000 | Fine et al. |
| 5,823,950 A | 10/1998 | Diab et al. | 6,035,223 A | 3/2000 | Baker, Jr. |
| 5,823,952 A | 10/1998 | Levinson et al. | 6,036,642 A | 3/2000 | Diab et al. |
| 5,827,179 A | 10/1998 | Lichter et al. | 6,041,247 A | 3/2000 | Weckstrom et al. |
| 5,827,182 A | 10/1998 | Raley et al. | 6,044,283 A | 3/2000 | Fein et al. |
| 5,829,439 A | 11/1998 | Yokosawa et al. | 6,047,201 A | 4/2000 | Jackson, III |
| 5,830,135 A | 11/1998 | Bosque et al. | 6,055,447 A | 4/2000 | Weil |
| 5,830,136 A | 11/1998 | DeLonzor et al. | 6,061,584 A | 5/2000 | Lovejoy et al. |
| 5,830,137 A | 11/1998 | Scharf | 6,064,898 A | 5/2000 | Aldrich |
| 5,839,439 A | 11/1998 | Nierlich et al. | 6,064,899 A | 5/2000 | Fein et al. |
| 5,842,979 A | 12/1998 | Jarman et al. | 6,067,462 A | 5/2000 | Diab et al. |
| 5,842,981 A | 12/1998 | Larsen et al. | 6,073,038 A | 6/2000 | Wang et al. |
| 5,842,982 A | 12/1998 | Mannheimer | 6,078,829 A | 6/2000 | Uchida |
| 5,846,190 A | 12/1998 | Woehrle | 6,078,833 A | 6/2000 | Hueber |
| 5,851,178 A | 12/1998 | Aronow | 6,081,735 A | 6/2000 | Diab et al. |
| 5,851,179 A | 12/1998 | Ritson et al. | 6,083,157 A | 7/2000 | Noller |
| 5,853,364 A | 12/1998 | Baker, Jr. et al. | 6,083,172 A | 7/2000 | Baker, Jr. et al. |
| 5,860,919 A | 1/1999 | Kiani-Azarbayjany et al. | 6,088,607 A | 7/2000 | Diab et al. |
| 5,865,736 A | 2/1999 | Baker, Jr. et al. | 6,094,592 A | 7/2000 | Yorkey et al. |
| 5,879,294 A | 3/1999 | Anderson et al. | 6,095,974 A | 8/2000 | Shemwell et al. |
| 5,885,213 A | 3/1999 | Richardson et al. | 6,104,938 A | 8/2000 | Huiku et al. |
| 5,890,929 A | 4/1999 | Mills et al. | 6,104,939 A | 8/2000 | Groner |
| 5,891,021 A | 4/1999 | Dillon et al. | 6,112,107 A | 8/2000 | Hannula |
| 5,891,022 A | 4/1999 | Pologe | 6,113,541 A | 9/2000 | Dias et al. |
| 5,891,024 A | 4/1999 | Jarman et al. | 6,115,621 A | 9/2000 | Chin |
| 5,891,025 A | 4/1999 | Buschmann et al. | 6,122,535 A | 9/2000 | Kaestle et al. |
| 5,891,026 A | 4/1999 | Wang et al. | 6,133,994 A | 10/2000 | Mathews et al. |
| 5,902,235 A | 5/1999 | Lewis et al. | 6,135,952 A | 10/2000 | Coetzee |
| 5,910,108 A | 6/1999 | Solenberger | 6,144,444 A | 11/2000 | Haworth et al. |
| 5,911,690 A | 6/1999 | Rall | 6,144,867 A | 11/2000 | Walker et al. |
| 5,912,656 A | 6/1999 | Tham et al. | 6,144,868 A | 11/2000 | Parker |
| 5,913,819 A | 6/1999 | Taylor et al. | 6,149,481 A | 11/2000 | Wang et al. |
| 5,916,154 A | 6/1999 | Hobbs et al. | 6,151,107 A | 11/2000 | Schöllermann et al. |
| 5,916,155 A | 6/1999 | Levinson et al. | 6,151,516 A | 11/2000 | Kiani-Azarbayjany et al. |
| 5,919,133 A | 7/1999 | Taylor et al. | 6,151,518 A | 11/2000 | Hayashi |
| 5,919,134 A | 7/1999 | Diab | 6,152,754 A | 11/2000 | Gerhardt et al. |
| 5,920,263 A | 7/1999 | Huttenhoff et al. | 6,154,667 A | 11/2000 | Miura et al. |
| 5,921,921 A | 7/1999 | Potratz et al. | 6,157,850 A | 12/2000 | Diab et al. |
| 5,922,607 A | 7/1999 | Bernreuter | 6,159,147 A | 12/2000 | Lichter |
| 5,924,979 A | 7/1999 | Swedlow et al. | 6,163,715 A | 12/2000 | Larsen et al. |
| 5,924,980 A | 7/1999 | Coetzee | 6,165,005 A | 12/2000 | Mills et al. |
| 5,924,982 A | 7/1999 | Chin | 6,173,196 B1 | 1/2001 | Delonzor et al. |
| 5,924,985 A | 7/1999 | Jones | 6,178,343 B1 | 1/2001 | Bindszus et al. |
| 5,934,277 A | 8/1999 | Mortz | 6,179,159 B1 | 1/2001 | Gurley |
| 5,934,925 A | 8/1999 | Tobler et al. | 6,181,958 B1 | 1/2001 | Steuer et al. |
| 5,940,182 A | 8/1999 | Lepper, Jr. et al. | 6,181,959 B1 | 1/2001 | Schöllermann et al. |
| 5,954,644 A | 9/1999 | Dettling et al. | 6,184,521 B1 | 2/2001 | Coffin, IV et al. |
| 5,957,840 A | 9/1999 | Terasawa et al. | 6,188,470 B1 | 2/2001 | Grace |
| 5,960,610 A | 10/1999 | Levinson et al. | 6,192,260 B1 | 2/2001 | Chance |
| 5,961,450 A | 10/1999 | Merchant et al. | 6,195,575 B1 | 2/2001 | Levinson |
| 5,961,452 A | 10/1999 | Chung et al. | 6,198,951 B1 | 3/2001 | Kosuda et al. |
| 5,964,701 A | 10/1999 | Asada et al. | 6,206,830 B1 | 3/2001 | Diab et al. |
| 5,971,930 A | 10/1999 | Elghazzawi | 6,213,952 B1 | 4/2001 | Finarov et al. |
| 5,978,691 A | 11/1999 | Mills | 6,217,523 B1 | 4/2001 | Amano et al. |
| 5,978,693 A | 11/1999 | Hamilton et al. | 6,222,189 B1 | 4/2001 | Misner et al. |
| 5,983,120 A | 11/1999 | Groner et al. | 6,223,064 B1 | 4/2001 | Lynn |
| 5,983,122 A | 11/1999 | Jarman et al. | 6,226,539 B1 | 5/2001 | Potratz |

| | | | | | | |
|---|---|---|---|---|---|---|
| 6,226,540 | B1 | 5/2001 | Bernreuter et al. | 6,453,184 | B1 | 9/2002 | Hyogo et al. |
| 6,229,856 | B1 | 5/2001 | Diab et al. | 6,456,862 | B2 | 9/2002 | Benni |
| 6,230,035 | B1 | 5/2001 | Aoyagi et al. | 6,461,305 | B1 | 10/2002 | Schnall |
| 6,233,470 | B1 | 5/2001 | Tsuchiya | 6,463,310 | B1 | 10/2002 | Swedlow et al. |
| 6,236,871 | B1 | 5/2001 | Tsuchiya | 6,463,311 | B1 | 10/2002 | Diab |
| 6,236,872 | B1 | 5/2001 | Diab et al. | 6,466,808 | B1 | 10/2002 | Chin et al. |
| 6,240,305 | B1 | 5/2001 | Tsuchiya | 6,466,809 | B1 | 10/2002 | Riley |
| 6,253,097 | B1 | 6/2001 | Aronow et al. | 6,470,199 | B1 | 10/2002 | Kopotic et al. |
| 6,253,098 | B1 | 6/2001 | Walker et al. | 6,470,200 | B1 | 10/2002 | Walker et al. |
| 6,256,523 | B1 | 7/2001 | Diab et al. | 6,480,729 | B2 | 11/2002 | Stone |
| 6,256,524 | B1 | 7/2001 | Walker et al. | 6,490,466 | B1 | 12/2002 | Fein et al. |
| 6,261,236 | B1 | 7/2001 | Grimblatov | 6,493,568 | B1 | 12/2002 | Bell |
| 6,263,221 | B1 | 7/2001 | Chance et al. | 6,496,711 | B1 | 12/2002 | Athan et al. |
| 6,263,222 | B1 | 7/2001 | Diab et al. | 6,498,942 | B1 | 12/2002 | Esenaliev et al. |
| 6,263,223 | B1 | 7/2001 | Shepherd et al. | 6,501,974 | B2 | 12/2002 | Huiku |
| 6,266,546 | B1 | 7/2001 | Steuer et al. | 6,501,975 | B2 | 12/2002 | Diab et al. |
| 6,266,547 | B1 | 7/2001 | Walker et al. | 6,505,060 | B1 | 1/2003 | Norris |
| 6,272,363 | B1 | 8/2001 | Casciani et al. | 6,505,061 | B2 | 1/2003 | Larson |
| 6,278,522 | B1 | 8/2001 | Lepper, Jr. et al. | 6,505,133 | B1 | 1/2003 | Hanna et al. |
| 6,280,213 | B1 | 8/2001 | Tobler et al. | 6,510,329 | B2 | 1/2003 | Heckel |
| 6,280,381 | B1 | 8/2001 | Malin et al. | 6,510,331 | B1 | 1/2003 | Williams et al. |
| 6,285,894 | B1 | 9/2001 | Oppelt et al. | 6,512,937 | B2 | 1/2003 | Blank et al. |
| 6,285,895 | B1 | 9/2001 | Ristolainen et al. | 6,515,273 | B2 | 2/2003 | Al-Ali |
| 6,285,896 | B1 | 9/2001 | Tobler et al. | 6,519,484 | B1 | 2/2003 | Lovejoy et al. |
| 6,298,252 | B1 | 10/2001 | Kovach et al. | 6,519,486 | B1 | 2/2003 | Edgar, Jr. et al. |
| 6,308,089 | B1 | 10/2001 | Von der Ruhr et al. | 6,519,487 | B1 | 2/2003 | Parker |
| 6,321,100 | B1 | 11/2001 | Parker | 6,525,386 | B1 | 2/2003 | Mills et al. |
| 6,330,468 | B1 | 12/2001 | Scharf | 6,526,300 | B1 | 2/2003 | Kiani et al. |
| 6,334,065 | B1 | 12/2001 | Al-Ali et al. | 6,526,301 | B2 | 2/2003 | Larsen et al. |
| 6,339,715 | B1 | 1/2002 | Bahr et al. | 6,541,756 | B2 | 4/2003 | Schulz et al. |
| 6,342,039 | B1 | 1/2002 | Lynn | 6,542,764 | B1 | 4/2003 | Al-Ali et al. |
| 6,343,223 | B1 | 1/2002 | Chin et al. | 6,546,267 | B1 | 4/2003 | Sugiura et al. |
| 6,343,224 | B1 | 1/2002 | Parker | 6,553,241 | B2 | 4/2003 | Mannheimer et al. |
| 6,349,228 | B1 | 2/2002 | Kiani et al. | 6,553,242 | B1 | 4/2003 | Sarussi |
| 6,351,658 | B1 | 2/2002 | Middleman et al. | 6,553,243 | B2 | 4/2003 | Gurley |
| 6,353,750 | B1 | 3/2002 | Kimura | 6,554,788 | B1 | 4/2003 | Hunley |
| 6,356,774 | B1 | 3/2002 | Bernstein et al. | 6,556,852 | B1 | 4/2003 | Schulze et al. |
| 6,360,113 | B1 | 3/2002 | Dettling | 6,560,470 | B1 | 5/2003 | Pologe |
| 6,360,114 | B1 | 3/2002 | Diab et al. | 6,564,077 | B2 | 5/2003 | Mortara |
| 6,361,501 | B1 | 3/2002 | Amano et al. | 6,564,088 | B1 | 5/2003 | Soller et al. |
| 6,363,269 | B1 | 3/2002 | Hanna et al. | 6,571,113 | B1 | 5/2003 | Fein et al. |
| D455,834 | S | 4/2002 | Donars et al. | 6,571,114 | B1 | 5/2003 | Koike et al. |
| 6,370,408 | B1 | 4/2002 | Merchant et al. | 6,574,491 | B2 | 6/2003 | Elghazzawi |
| 6,370,409 | B1 | 4/2002 | Chung et al. | 6,580,086 | B1 | 6/2003 | Schulz et al. |
| 6,371,921 | B1 | 4/2002 | Caro | 6,583,987 | B2 * | 6/2003 | Skinner et al. ............... 361/704 |
| 6,374,129 | B1 | 4/2002 | Chin et al. | 6,584,336 | B1 | 6/2003 | Ali et al. |
| 6,377,829 | B1 | 4/2002 | Al-Ali et al. | 6,587,703 | B2 | 7/2003 | Cheng et al. |
| 6,381,479 | B1 | 4/2002 | Norris | 6,587,704 | B1 | 7/2003 | Fine et al. |
| 6,381,480 | B1 | 4/2002 | Stoddar et al. | 6,589,172 | B2 | 7/2003 | Williams et al. |
| 6,385,471 | B1 | 5/2002 | Mortz | 6,591,122 | B2 | 7/2003 | Schmitt |
| 6,385,821 | B1 | 5/2002 | Modgil et al. | 6,591,123 | B2 | 7/2003 | Fein et al. |
| 6,388,240 | B2 | 5/2002 | Schulz et al. | 6,594,511 | B2 | 7/2003 | Stone et al. |
| 6,393,310 | B1 | 5/2002 | Kuenster | 6,594,512 | B2 | 7/2003 | Huang |
| 6,393,311 | B1 | 5/2002 | Edgar, Jr. et al. | 6,594,513 | B1 | 7/2003 | Jobsis et al. |
| 6,397,091 | B2 | 5/2002 | Diab et al. | 6,597,931 | B1 | 7/2003 | Cheng et al. |
| 6,397,092 | B1 | 5/2002 | Norris et al. | 6,597,933 | B2 | 7/2003 | Kiani et al. |
| 6,397,093 | B1 | 5/2002 | Aldrich | 6,600,940 | B1 | 7/2003 | Fein et al. |
| 6,400,971 | B1 | 6/2002 | Finarov et al. | 6,606,510 | B2 | 8/2003 | Swedlow et al. |
| 6,400,972 | B1 | 6/2002 | Fine | 6,606,511 | B1 | 8/2003 | Ali et al. |
| 6,400,973 | B1 | 6/2002 | Winter | 6,606,512 | B2 | 8/2003 | Muz et al. |
| 6,402,690 | B1 | 6/2002 | Rhee et al. | 6,608,562 | B1 | 8/2003 | Kimura et al. |
| 6,408,198 | B1 | 6/2002 | Hanna et al. | 6,609,016 | B1 | 8/2003 | Lynn |
| 6,411,832 | B1 | 6/2002 | Guthermann | 6,615,064 | B1 | 9/2003 | Aldrich |
| 6,411,833 | B1 | 6/2002 | Baker, Jr. et al. | 6,615,065 | B1 | 9/2003 | Barrett et al. |
| 6,421,549 | B1 | 7/2002 | Jacques | 6,618,602 | B2 | 9/2003 | Levin et al. |
| 6,430,423 | B2 | 8/2002 | DeLonzor et al. | 6,622,034 | B1 | 9/2003 | Gorski et al. |
| 6,430,513 | B1 | 8/2002 | Wang et al. | 6,628,975 | B1 | 9/2003 | Fein et al. |
| 6,430,525 | B1 | 8/2002 | Weber et al. | 6,631,281 | B1 | 10/2003 | Kästle |
| 6,434,408 | B1 | 8/2002 | Heckel et al. | 6,632,181 | B2 | 10/2003 | Flaherty |
| 6,438,396 | B1 | 8/2002 | Cook | 6,640,116 | B2 | 10/2003 | Diab |
| 6,438,399 | B1 | 8/2002 | Kurth | 6,643,530 | B2 | 11/2003 | Diab et al. |
| 6,449,501 | B1 | 9/2002 | Reuss | 6,643,531 | B1 | 11/2003 | Katarow |
| 6,453,183 | B1 | 9/2002 | Walker | 6,647,279 | B2 | 11/2003 | Pologe |

| | | |
|---|---|---|
| 6,647,280 B2 | 11/2003 | Bahr et al. |
| 6,650,916 B2 | 11/2003 | Cook |
| 6,650,917 B2 | 11/2003 | Diab et al. |
| 6,650,918 B2 | 11/2003 | Terry |
| 6,654,622 B1 | 11/2003 | Eberhard et al. |
| 6,654,623 B1 | 11/2003 | Kästle |
| 6,654,624 B2 | 11/2003 | Diab et al. |
| 6,658,276 B2 | 12/2003 | Kianl et al. |
| 6,658,277 B2 | 12/2003 | Wasserman |
| 6,662,033 B2 | 12/2003 | Casciani et al. |
| 6,665,551 B1 | 12/2003 | Suzuki |
| 6,668,182 B2 | 12/2003 | Hubelbank |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,671,530 B2 | 12/2003 | Chung et al. |
| 6,671,531 B2 | 12/2003 | Al-Ali et al. |
| 6,671,532 B1 | 12/2003 | Fudge et al. |
| 6,675,031 B1 | 1/2004 | Porges et al. |
| 6,678,543 B2 | 1/2004 | Diab et al. |
| 6,681,126 B2 | 1/2004 | Solenberger |
| 6,681,128 B2 | 1/2004 | Steuer et al. |
| 6,681,454 B2 | 1/2004 | Modgil et al. |
| 6,684,090 B2 | 1/2004 | Ali et al. |
| 6,684,091 B2 | 1/2004 | Parker |
| 6,694,160 B2 | 2/2004 | Chin |
| 6,697,653 B2 | 2/2004 | Hanna |
| 6,697,655 B2 | 2/2004 | Sueppel et al. |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,699,199 B2 | 3/2004 | Asada et al. |
| 6,701,170 B2 | 3/2004 | Stetson |
| 6,702,752 B2 | 3/2004 | Dekker |
| 6,707,257 B2 | 3/2004 | Norris |
| 6,708,049 B1 | 3/2004 | Berson et al. |
| 6,709,402 B2 | 3/2004 | Dekker |
| 6,711,424 B1 | 3/2004 | Fine et al. |
| 6,711,425 B1 | 3/2004 | Reuss |
| 6,712,762 B1 | 3/2004 | Lichter |
| 6,714,803 B1 | 3/2004 | Mortz |
| 6,714,804 B2 | 3/2004 | Al-Ali et al. |
| 6,714,805 B2 | 3/2004 | Jeon et al. |
| RE38,492 E | 4/2004 | Diab et al. |
| 6,719,686 B2 | 4/2004 | Coakley et al. |
| 6,719,705 B2 | 4/2004 | Mills |
| 6,720,734 B2 | 4/2004 | Norris |
| 6,721,584 B2 | 4/2004 | Baker, Jr. et al. |
| 6,721,585 B1 | 4/2004 | Parker |
| 6,725,074 B1 | 4/2004 | Kästle |
| 6,725,075 B2 | 4/2004 | Al-Ali |
| 6,731,962 B1 | 5/2004 | Katarow |
| 6,731,963 B2 | 5/2004 | Finarov et al. |
| 6,731,967 B1 | 5/2004 | Turcott |
| 6,735,459 B2 | 5/2004 | Parker |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | O'Neill et al. |
| 6,754,515 B1 | 6/2004 | Pologe |
| 6,754,516 B2 | 6/2004 | Mannheimer |
| 6,760,607 B2 | 7/2004 | Al-All |
| 6,760,609 B2 | 7/2004 | Jacques |
| 6,760,610 B2 | 7/2004 | Tschupp et al. |
| 6,763,255 B2 | 7/2004 | DeLonzor et al. |
| 6,763,256 B2 | 7/2004 | Kimball et al. |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,791,689 B1 | 9/2004 | Weckstrom |
| 6,792,300 B1 | 9/2004 | Diab et al. |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,801,802 B2 | 10/2004 | Sitzman et al. |
| 6,802,812 B1 | 10/2004 | Walker et al. |
| 6,805,673 B2 | 10/2004 | Dekker |
| 6,810,277 B2 | 10/2004 | Edgar, Jr. et al. |
| 6,813,511 B2 | 11/2004 | Diab et al. |
| 6,816,266 B2 | 11/2004 | Varshneya et al. |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |
| 6,830,711 B2 | 12/2004 | Mills et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |
| 6,839,659 B2 | 1/2005 | Tarassenko et al. |
| 6,842,635 B1 | 1/2005 | Parker |
| 6,845,256 B2 | 1/2005 | Chin et al. |
| 6,850,787 B2 | 2/2005 | Weber et al. |
| 6,850,788 B2 | 2/2005 | Al-Ali |
| 6,850,789 B2 | 2/2005 | Schweitzer, Jr. et al. |
| 6,861,639 B2 | 3/2005 | Al-Ali |
| 6,863,652 B2 | 3/2005 | Huang et al. |
| 6,865,407 B2 | 3/2005 | Kimball et al. |
| 6,879,850 B2 | 4/2005 | Kimball |
| 6,882,874 B2 | 4/2005 | Huiku |
| 6,898,452 B2 | 5/2005 | Al-Ali et al. |
| 6,909,912 B2 | 6/2005 | Melker et al. |
| 6,912,413 B2 | 6/2005 | Rantala et al. |
| 6,916,289 B2 | 7/2005 | Schnall |
| 6,920,345 B2 | 7/2005 | Al-Ali et al. |
| 6,931,269 B2 | 8/2005 | Terry |
| 6,934,570 B2 | 8/2005 | Kiani et al. |
| 6,941,162 B2 | 9/2005 | Fudge et al. |
| 6,947,781 B2 | 9/2005 | Asada et al. |
| 6,950,687 B2 | 9/2005 | Al-Ali |
| 6,954,664 B2 | 10/2005 | Sweitzer |
| 6,963,767 B2 | 11/2005 | Rantala et al. |
| 6,968,221 B2 | 11/2005 | Rosenthal |
| 6,979,812 B2 | 12/2005 | Al-Ali |
| 6,983,178 B2 | 1/2006 | Fine et al. |
| 6,985,763 B2 | 1/2006 | Boas et al. |
| 6,985,764 B2 | 1/2006 | Mason et al. |
| 6,990,426 B2 | 1/2006 | Yoon et al. |
| 6,992,751 B2 | 1/2006 | Al-Ali et al. |
| 6,992,772 B2 | 1/2006 | Block et al. |
| 6,993,371 B2 | 1/2006 | Kiani et al. |
| 6,993,372 B2 | 1/2006 | Fine et al. |
| 6,996,427 B2 | 2/2006 | Ali et al. |
| 7,003,338 B2 | 2/2006 | Weber et al. |
| 7,003,339 B2 | 2/2006 | Diab et al. |
| 7,006,855 B1 | 2/2006 | Sarussi |
| 7,006,856 B2 | 2/2006 | Baker, Jr. et al. |
| 7,016,715 B2 | 3/2006 | Stetson |
| 7,020,507 B2 | 3/2006 | Scharf et al. |
| 7,024,233 B2 | 4/2006 | Ali et al. |
| 7,024,235 B2 | 4/2006 | Melker et al. |
| 7,025,728 B2 | 4/2006 | Ito et al. |
| 7,027,849 B2 | 4/2006 | Al-Ali et al. |
| 7,027,850 B2 | 4/2006 | Wasserman |
| 7,039,449 B2 | 5/2006 | Al-Ali |
| 7,043,289 B2 | 5/2006 | Fine et al. |
| 7,047,054 B2 | 5/2006 | Benni |
| 7,047,055 B2 | 5/2006 | Boas et al. |
| 7,047,056 B2 | 5/2006 | Hannula et al. |
| 7,060,035 B2 | 6/2006 | Wasserman et al. |
| 7,062,307 B2 | 6/2006 | Norris et al. |

| | | | | | |
|---|---|---|---|---|---|
| 7,067,893 B2 | 6/2006 | Mills et al. | 2004/0024297 A1 | 2/2004 | Chen et al. |
| 7,072,701 B2 | 7/2006 | Chen et al. | 2004/0024326 A1 | 2/2004 | Yeo et al. |
| 7,072,702 B2 | 7/2006 | Edgar, Jr. et al. | 2004/0034293 A1 | 2/2004 | Kimball |
| 7,079,880 B2 | 7/2006 | Stetson | 2004/0039272 A1 | 2/2004 | Abdul-Hafiz et al. |
| 7,085,597 B2 | 8/2006 | Fein et al. | 2004/0039273 A1 | 2/2004 | Terry |
| 7,096,052 B2 | 8/2006 | Mason et al. | 2004/0054269 A1 | 3/2004 | Rantala et al. |
| 7,096,054 B2 | 8/2006 | Abdul-Hafiz et al. | 2004/0054291 A1 | 3/2004 | Schulz et al. |
| 7,107,088 B2 | 9/2006 | Aceti | 2004/0059209 A1 | 3/2004 | Al-Ali et al. |
| 7,113,815 B2 | 9/2006 | O'Neil et al. | 2004/0059210 A1 | 3/2004 | Stetson |
| 7,123,950 B2 | 10/2006 | Mannheimer | 2004/0064020 A1 | 4/2004 | Diab et al. |
| 7,127,278 B2 | 10/2006 | Melker et al. | 2004/0068164 A1 | 4/2004 | Diab et al. |
| 7,130,671 B2 | 10/2006 | Baker, Jr. et al. | 2004/0087846 A1 | 5/2004 | Wasserman |
| 7,132,641 B2 | 11/2006 | Schulz et al. | 2004/0092805 A1 | 5/2004 | Yarita |
| 7,133,711 B2 | 11/2006 | Chernoguz et al. | 2004/0097797 A1 | 5/2004 | Porges et al. |
| 7,139,599 B2 | 11/2006 | Terry | 2004/0098009 A1 | 5/2004 | Boecker et al. |
| 7,142,901 B2 | 11/2006 | Kiani et al. | 2004/0107065 A1 | 6/2004 | Al-Ali et al. |
| 7,190,986 B1 * | 3/2007 | Hannula et al. ............. 600/344 | 2004/0116788 A1 | 6/2004 | Chernoguz et al. |
| 7,190,987 B2 | 3/2007 | Lindekugel et al. | 2004/0116789 A1 | 6/2004 | Boas et al. |
| 7,198,778 B2 | 4/2007 | Mannheimer et al. | 2004/0117891 A1 | 6/2004 | Hannula et al. |
| 7,215,984 B2 | 5/2007 | Diab et al. | 2004/0122300 A1 | 6/2004 | Boas et al. |
| 7,225,006 B2 | 5/2007 | Al-Ali et al. | 2004/0122302 A1 | 6/2004 | Mason et al. |
| 7,228,161 B2 | 6/2007 | Chin | 2004/0133087 A1 | 7/2004 | Ali et al. |
| 7,236,811 B2 | 6/2007 | Schmitt | 2004/0133088 A1 | 7/2004 | Al-Ali et al. |
| 7,248,910 B2 | 7/2007 | Li et al. | 2004/0138538 A1 | 7/2004 | Stetson |
| 7,254,433 B2 | 8/2007 | Diab et al. | 2004/0138540 A1 | 7/2004 | Baker, Jr. et al. |
| 7,254,434 B2 | 8/2007 | Schulz et al. | 2004/0143172 A1 | 7/2004 | Fudge et al. |
| 7,280,858 B2 | 10/2007 | Al-Ali et al. | 2004/0147821 A1 | 7/2004 | Al-Ali et al. |
| 7,289,837 B2 | 10/2007 | Mannheimer et al. | 2004/0147822 A1 | 7/2004 | Al-Ali et al. |
| 7,295,866 B2 | 11/2007 | Al-Ali et al. | 2004/0147823 A1 | 7/2004 | Kiani et al. |
| 7,305,262 B2 | 12/2007 | Brodnick et al. | 2004/0147824 A1 | 7/2004 | Diab et al. |
| 7,313,427 B2 | 12/2007 | Benni | 2004/0152965 A1 | 8/2004 | Diab et al. |
| 7,315,753 B2 | 1/2008 | Baker, Jr. et al. | 2004/0158134 A1 | 8/2004 | Diab et al. |
| 7,340,287 B2 | 3/2008 | Mason et al. | 2004/0158135 A1 | 8/2004 | Baker, Jr. et al. |
| 2001/0021803 A1 | 9/2001 | Blank et al. | 2004/0162472 A1 | 8/2004 | Berson et al. |
| 2001/0051767 A1 | 12/2001 | Williams et al. | 2004/0167381 A1 | 8/2004 | Lichter |
| 2002/0016537 A1 | 2/2002 | Muz et al. | 2004/0171920 A1 | 9/2004 | Mannheimer et al. |
| 2002/0026109 A1 | 2/2002 | Diab et al. | 2004/0171948 A1 | 9/2004 | Terry |
| 2002/0028990 A1 | 3/2002 | Shepherd et al. | 2004/0176671 A1 | 9/2004 | Fine et al. |
| 2002/0038078 A1 | 3/2002 | Ito | 2004/0181133 A1 | 9/2004 | Al-Ali et al. |
| 2002/0042558 A1 | 4/2002 | Mendelson | 2004/0181134 A1 | 9/2004 | Baker, Jr. et al. |
| 2002/0068859 A1 | 6/2002 | Knopp | 2004/0186358 A1 | 9/2004 | Chernow et al. |
| 2002/0072681 A1 | 6/2002 | Schnali | 2004/0199063 A1 | 10/2004 | O'Neil et al. |
| 2002/0116797 A1 | 8/2002 | Modgil et al. | 2004/0204636 A1 | 10/2004 | Diab et al. |
| 2002/0128544 A1 | 9/2002 | Diab et al. | 2004/0204637 A1 | 10/2004 | Diab et al. |
| 2002/0133067 A1 | 9/2002 | Jackson, III | 2004/0204865 A1 | 10/2004 | Lee et al. |
| 2002/0156354 A1 | 10/2002 | Larson | 2004/0210146 A1 | 10/2004 | Diab et al. |
| 2002/0165440 A1 | 11/2002 | Mason et al. | 2004/0215069 A1 | 10/2004 | Mannheimer |
| 2002/0173706 A1 | 11/2002 | Takatani | 2004/0215085 A1 | 10/2004 | Schnall |
| 2002/0173709 A1 | 11/2002 | Fine et al. | 2004/0230107 A1 | 11/2004 | Asada et al. |
| 2002/0190863 A1 | 12/2002 | Lynn | 2004/0230108 A1 | 11/2004 | Melker et al. |
| 2002/0198442 A1 | 12/2002 | Rantala et al. | 2004/0236196 A1 | 11/2004 | Diab et al. |
| 2003/0018243 A1 | 1/2003 | Gerhardt et al. | 2004/0242980 A1 | 12/2004 | Kiani et al. |
| 2003/0036690 A1 | 2/2003 | Geddes et al. | 2004/0249252 A1 | 12/2004 | Fine et al. |
| 2003/0045785 A1 | 3/2003 | Diab et al. | 2004/0257557 A1 | 12/2004 | Block et al. |
| 2003/0073889 A1 | 4/2003 | Keilbach et al. | 2004/0260161 A1 | 12/2004 | Melker et al. |
| 2003/0073890 A1 | 4/2003 | Hanna | 2004/0267103 A1 | 12/2004 | Li et al. |
| 2003/0100840 A1 | 5/2003 | Sugiura et al. | 2004/0267104 A1 | 12/2004 | Hannula et al. |
| 2003/0132495 A1 | 7/2003 | Mills et al. | 2004/0267140 A1 | 12/2004 | Ito et al. |
| 2003/0135099 A1 | 7/2003 | Al-Ali | 2005/0004479 A1 | 1/2005 | Townsend et al. |
| 2003/0162414 A1 | 8/2003 | Schulz et al. | 2005/0010092 A1 | 1/2005 | Weber et al. |
| 2003/0171662 A1 | 9/2003 | O'Connor et al. | 2005/0014999 A1 | 1/2005 | Rahe-Meyer |
| 2003/0176776 A1 | 9/2003 | Huiku | 2005/0020887 A1 | 1/2005 | Goldberg |
| 2003/0181799 A1 | 9/2003 | Lindekugel et al. | 2005/0020894 A1 | 1/2005 | Norris et al. |
| 2003/0187337 A1 | 10/2003 | Tarassenko et al. | 2005/0033131 A1 | 2/2005 | Chen |
| 2003/0195402 A1 | 10/2003 | Fein et al. | 2005/0043599 A1 | 2/2005 | O'Mara |
| 2003/0197679 A1 | 10/2003 | Ali et al. | 2005/0043600 A1 | 2/2005 | Diab et al. |
| 2003/0212316 A1 | 11/2003 | Leiden et al. | 2005/0049468 A1 | 3/2005 | Carlson |
| 2003/0225323 A1 | 12/2003 | Kiani et al. | 2005/0049470 A1 | 3/2005 | Terry |
| 2003/0225337 A1 | 12/2003 | Scharf et al. | 2005/0049471 A1 | 3/2005 | Aceti |
| 2003/0236452 A1 | 12/2003 | Melker et al. | 2005/0070773 A1 | 3/2005 | Chin |
| 2003/0236647 A1 | 12/2003 | Yoon et al. | 2005/0070776 A1 | 3/2005 | Mannheimer et al. |
| 2004/0006261 A1 | 1/2004 | Swedlow et al. | 2005/0075546 A1 | 4/2005 | Samsoondar |
| 2004/0010188 A1 | 1/2004 | Wasserman et al. | 2005/0075550 A1 | 4/2005 | Lindekugel |

| | | | | | | |
|---|---|---|---|---|---|---|
| 2005/0085704 A1 | 4/2005 | Schulz | | EP | 00630203 | 9/1993 |
| 2005/0090720 A1 | 4/2005 | Wu | | EP | 0 572 684 | 12/1993 |
| 2005/0197548 A1 | 9/2005 | Dietiker | | EP | 00615723 | 9/1994 |
| 2005/0228248 A1 | 10/2005 | Dietiker | | EP | 00702931 | 3/1996 |
| 2005/0256386 A1 | 11/2005 | Chan | | EP | 00724860 | 8/1996 |
| 2005/0277819 A1 | 12/2005 | Kiani | | EP | 00793942 | 9/1997 |
| 2006/0020179 A1 | 1/2006 | Anderson | | EP | 0 864 293 | 9/1998 |
| 2006/0030764 A1 | 2/2006 | Porges | | EP | 01006863 | 10/1998 |
| 2006/0058594 A1 | 3/2006 | Ishizuka et al. | | EP | 01006864 | 10/1998 |
| 2006/0074280 A1 | 4/2006 | Martis | | EP | 0875199 | 11/1998 |
| 2006/0084852 A1 | 4/2006 | Mason et al. | | EP | 00998214 | 12/1998 |
| 2006/0084878 A1 | 4/2006 | Banet | | EP | 0898933 | 3/1999 |
| 2006/0089547 A1 | 4/2006 | Sarussi | | EP | 01332713 | 8/2003 |
| 2006/0106294 A1 | 5/2006 | Maser et al. | | EP | 01469773 | 8/2003 |
| 2006/0122517 A1 | 6/2006 | Banet | | EP | 1502529 | 7/2004 |
| 2006/0129039 A1 | 6/2006 | Lindner | | EP | 1491135 | 12/2004 |
| 2006/0155198 A1 | 7/2006 | Schmid | | EP | 1584287 | 12/2005 |
| 2006/0173257 A1 | 8/2006 | Nagai | | FR | 2685865 | 1/1992 |
| 2006/0195028 A1 | 8/2006 | Hannula et al. | | GB | 2 259 545 | 3/1993 |
| 2006/0224053 A1 | 10/2006 | Black et al. | | JP | 63275325 A | 11/1988 |
| 2006/0253007 A1 | 11/2006 | Cheng et al. | | JP | 2013450 | 1/1990 |
| 2006/0264722 A1 | 11/2006 | Hannula et al. | | JP | 2111343 | 4/1990 |
| 2006/0264723 A1 | 11/2006 | Hannula et al. | | JP | 02-191434 | 7/1990 |
| 2006/0264724 A1 | 11/2006 | Hannula et al. | | JP | 2237544 | 9/1990 |
| 2006/0264725 A1 | 11/2006 | Hannula et al. | | JP | 03-173536 | 7/1991 |
| 2006/0264726 A1 | 11/2006 | Mannheimer et al. | | JP | 3170866 | 7/1991 |
| 2006/0264727 A1 | 11/2006 | Mannheimer et al. | | JP | 3245042 | 10/1991 |
| 2006/0276700 A1 | 12/2006 | O'Neil et al. | | JP | 4174648 | 6/1992 |
| 2006/0281984 A1 | 12/2006 | Mannheimer et al. | | JP | 4191642 | 7/1992 |
| 2007/0032708 A1 | 2/2007 | Eghbal et al. | | JP | 4332536 | 11/1992 |
| 2007/0032709 A1 | 2/2007 | Coakley et al. | | JP | 3124073 | 3/1993 |
| 2007/0032710 A1 | 2/2007 | Raridan, Jr. et al. | | JP | 5049624 | 3/1993 |
| 2007/0032712 A1 | 2/2007 | Raridan et al. | | JP | 5049625 | 3/1993 |
| 2007/0073126 A1 | 3/2007 | Raridan, Jr. | | JP | 3115374 | 4/1993 |
| 2007/0078309 A1 | 4/2007 | Matlock | | JP | 2005/200031 | 8/1993 |
| 2007/0078315 A1 | 4/2007 | Kling et al. | | JP | 5212016 | 8/1993 |
| 2007/0078317 A1 | 4/2007 | Matlock | | JP | 06014906 | 1/1994 |
| 2007/0219440 A1 | 9/2007 | Hannula et al. | | JP | 6016774 | 3/1994 |
| 2008/0017800 A1 | 1/2008 | Benni | | JP | 3116255 | 4/1994 |
| 2008/0064940 A1 | 3/2008 | Raridan | | JP | 6029504 | 4/1994 |
| | | | | JP | 6098881 | 4/1994 |
| FOREIGN PATENT DOCUMENTS | | | | JP | 06-154177 | 6/1994 |
| DE | 3405444 | 8/1985 | | JP | 6269430 | 9/1994 |
| DE | 3516338 | 11/1986 | | JP | 6285048 | 10/1994 |
| DE | 37 03 458 | 8/1988 | | JP | 7001273 | 1/1995 |
| DE | 3938759 | 5/1991 | | JP | 7124138 | 5/1995 |
| DE | 4210102 | 9/1993 | | JP | 7136150 | 5/1995 |
| DE | 4423597 | 8/1995 | | JP | 3116259 | 6/1995 |
| DE | 19632361 | 2/1997 | | JP | 3116260 | 6/1995 |
| DE | 69123448 | 5/1997 | | JP | 7155311 | 6/1995 |
| DE | 19703220 | 7/1997 | | JP | 7155313 | 6/1995 |
| DE | 19640807 | 9/1997 | | JP | 3238813 | 7/1995 |
| DE | 19647877 | 4/1998 | | JP | 7171139 | 7/1995 |
| DE | 10030862 | 1/2002 | | JP | 3134144 | 9/1995 |
| DE | 20318882 | 4/2004 | | JP | 7236625 | 9/1995 |
| EP | 0127947 | 5/1984 | | JP | 7246191 | 9/1995 |
| EP | 00194105 B1 | 9/1986 | | JP | 8256996 | 10/1996 |
| EP | 00204459 | 12/1986 | | JP | 9192120 | 7/1997 |
| EP | 0204459 | 12/1986 | | JP | 10216113 | 8/1998 |
| EP | 0 262 779 | 4/1988 | | JP | 10216114 | 8/1998 |
| EP | 0315040 | 10/1988 | | JP | 10337282 | 12/1998 |
| EP | 0314331 | 5/1989 | | JP | 11019074 | 1/1999 |
| EP | 00352923 | 1/1990 | | JP | 11155841 | 6/1999 |
| EP | 0 360 977 | 4/1990 | | JP | 11-188019 | 7/1999 |
| EP | 00430340 | 6/1991 | | JP | 11244268 | 9/1999 |
| EP | 0435 500 | 7/1991 | | JP | 20107157 | 4/2000 |
| EP | 0572684 | 5/1992 | | JP | 20237170 | 9/2000 |
| EP | 00497021 | 8/1992 | | JP | 21245871 | 9/2001 |
| EP | 0529412 | 8/1992 | | JP | 22224088 | 8/2002 |
| EP | 0531631 | 9/1992 | | JP | 22282242 | 10/2002 |
| EP | 0566354 | 4/1993 | | JP | 23153881 | 5/2003 |
| EP | 0587009 | 8/1993 | | JP | 23153882 | 5/2003 |
| | | | | JP | 23169791 | 6/2003 |

| | | |
|---|---|---|
| JP | 23194714 | 7/2003 |
| JP | 23210438 | 7/2003 |
| JP | 23275192 | 9/2003 |
| JP | 23339678 | 12/2003 |
| JP | 24008572 | 1/2004 |
| JP | 24089546 | 3/2004 |
| JP | 24113353 | 4/2004 |
| JP | 24135854 | 5/2004 |
| JP | 24148069 | 5/2004 |
| JP | 24148070 | 5/2004 |
| JP | 24159810 | 6/2004 |
| JP | 24166775 | 6/2004 |
| JP | 24194908 | 7/2004 |
| JP | 24202190 | 7/2004 |
| JP | 24248819 | 9/2004 |
| JP | 24261364 | 9/2004 |
| JP | 24290412 | 10/2004 |
| JP | 24290544 | 10/2004 |
| JP | 24290545 | 10/2004 |
| JP | 24329406 | 11/2004 |
| JP | 24329607 | 11/2004 |
| JP | 24329928 | 11/2004 |
| JP | 04351107 | 12/2004 |
| JP | 24337605 | 12/2004 |
| JP | 24344367 | 12/2004 |
| JP | 0534472 | 2/2005 |
| WO | WO 98/09566 | 10/1989 |
| WO | WO 90/01293 | 2/1990 |
| WO | WO 90/04352 | 5/1990 |
| WO | WO 91/01678 | 2/1991 |
| WO | WO 91/11137 | 8/1991 |
| WO | WO 92/00513 | 1/1992 |
| WO | WO 92/21281 | 12/1992 |
| WO | WO 93/09711 | 5/1993 |
| WO | WO 93/13706 | 7/1993 |
| WO | WO 93/16629 | 9/1993 |
| WO | WO 94/03102 | 2/1994 |
| WO | WO 94/23643 | 10/1994 |
| WO | WO 95/02358 | 1/1995 |
| WO | WO 95/12349 | 5/1995 |
| WO | WO 95/16970 | 6/1995 |
| WO | WO 96/13208 | 5/1996 |
| WO | WO 96/39927 | 12/1996 |
| WO | WO 97/36536 | 10/1997 |
| WO | WO 97/36538 | 10/1997 |
| WO | 9746069 A | 12/1997 |
| WO | WO 97/49330 | 12/1997 |
| WO | WO 98/17174 | 4/1998 |
| WO | WO 98/18382 | 5/1998 |
| WO | WO 98/43071 | 10/1998 |
| WO | WO 9843071 | 10/1998 |
| WO | WO 98/51212 | 11/1998 |
| WO | WO 98/57577 | 12/1998 |
| WO | WO 99/00053 | 1/1999 |
| WO | WO 99/32030 | 7/1999 |
| WO | WO 99/47039 | 9/1999 |
| WO | WO 99/63884 | 12/1999 |
| WO | WO 00/21438 | 4/2000 |
| WO | WO 00/28888 | 5/2000 |
| WO | WO 00/59374 | 10/2000 |
| WO | WO 01/13790 | 3/2001 |
| WO | WO 01/16577 | 3/2001 |
| WO | WO 01/17421 | 3/2001 |
| WO | WO 01/47426 | 3/2001 |
| WO | WO 01/40776 | 6/2001 |
| WO | WO 01/67946 | 9/2001 |
| WO | WO 01/76461 | 10/2001 |
| WO | WO 02/14793 | 2/2002 |
| WO | WO 02/35999 | 5/2002 |
| WO | WO 02/062213 | 8/2002 |
| WO | WO 02/074162 | 9/2002 |
| WO | WO 02/085202 | 10/2002 |
| WO | WO 03/000125 | 1/2003 |
| WO | WO 03/001180 | 1/2003 |
| WO | WO 03/009750 | 2/2003 |
| WO | WO 03/011127 | 2/2003 |
| WO | WO 03/020129 | 3/2003 |
| WO | WO 03/039326 | 5/2003 |
| WO | WO 03/063697 | 8/2003 |
| WO | WO 03/073924 | 9/2003 |
| WO | WO 2004/000114 | 12/2003 |
| WO | WO 2004/006748 | 1/2004 |
| WO | WO 2004/069046 | 8/2004 |
| WO | WO 2004/075746 | 9/2004 |
| WO | WO 2005/002434 | 1/2005 |
| WO | WO 2005/009221 | 2/2005 |
| WO | WO 2005/010567 | 2/2005 |
| WO | WO 2005/010568 | 2/2005 |
| WO | 2005025399 | 3/2005 |
| WO | WO 2005/020120 | 3/2005 |
| WO | WO 2005/065540 | 7/2005 |
| WO | 2006097910 | 9/2006 |
| WO | WO 2006/104790 | 10/2006 |
| WO | 2007051066 | 5/2007 |

OTHER PUBLICATIONS

Rheineck-Leyssius, Aart t., et al.; "Advanced Pulse Oximeter Signal Processing Technology Compared to Simple Averaging: I. Effect on Frequency of Alarms in the Operating Room," *Journal of clinical Anestesia*, vol. 11, pp. 192-195 (1990).

Zahar, N., et al.; "Automatic Feedback Control of Oxygen Therapy Using Pulse Oximetry," *Annual International Conference of the IEEE Engineering in Medicine and Biology Society*, vol. 13, No. 4, pp. 1614-1615 (1991).

Aoyagi, T., et al.; "Analysis of Motion Artifacts in Pulse Oximetry," *Japanese Society ME*, vol. 42, p. 20 (1993) (Article in Japanese—contains English summary of article).

Barreto, A.B., et al.; "Adaptive Cancelation of Motion artifact in Photoplethysmographic Blood Volume Pulse Measurements for Exercise Evaluation," *IEEE-EMBC and CMBEC—Theme 4: Signal Processing*, pp. 983-984 (1995).

Vincente, L.M., et al.; "Adaptive Pre-Processing of Photoplethysmographic Blood Volume Pulse Measurements," pp. 114-117 (1996).

Plummer, John L., et al.; "Identification of Movement Artifact by the Nellcor N-200 and N-3000 Pulse Oximeters," *Journal of clinical Monitoring*, vol. 13, pp. 109-113 (1997).

Barnum, P.T., et al.; "Novel Pulse Oximetry Technology Capable of Reliable Bradycardia Monitoring in the Neonate," *Respiratory Care*, vol. 42, No. 1, p. 1072 (Nov. 1997).

Poets, C. F., et al.; "Detection of movement artifact in recorded pulse oximeter saturation," *Eur. J. Pediatr.*; vol. 156, pp. 808-811 (1997).

Masin, Donald I., et al.; "Fetal Transmission Pulse Oximetry," *Proceedings 19th International Conference IEEE/EMBS*, Oct. 30-Nov. 2, 1997; pp. 2326-2329.

Block, Frank E., Jr., et al.; "Technology evaluation report: Obtaining pulse oximeter signals when the usual probe cannot be used," *International journal of clinical Monitoring and Computing*, vol. 14, pp. 23-28 (1997).

Nijland, Roel, et al.; "Validation of Reflectance Pulse Oximetry: An Evaluation of a new Sensor in Piglets," *Journal of Clinical Monitoring*, vol. 13, pp. 43-49 (1997).

Soto, Denise A.; "A Comparative Study of Pulse Oximeter Measurements: Digit Versus Earlobe," Master of Science Thesis, California State University Dominguez Hills, May 1997, 46 pgs.

Faisst, Karin, et al.; "Intrapartum Reflectance Pulse Oximetry: Effects of Sensor Location and Fixation Duration on Oxygen Saturation Readings," *Journal of Clinical Monitoring*, vol. 13, pp. 299-302 (1997).

Izumi, Akio, et al.; "Accuracy and Utility of a New Reflectance Pulse Oximeter for Fetal Monitoring During Labor," *Journal of Clinical Monitoring*, vol. 13, pp. 103-108 (1997).

Mannheimer Paul D. 'et al.; "Wavelength Selection for Low-Saturation Pulse Oximetry," *IEEE Transactions on Biomedical Engineering*, vol. 44, No. 3, pp. 148-158 Mar. 1997.

"Smaller Product, Tighter Tolerances Pose Dispensing Challenges for Medical Device Manufacturer," *Adhesives Age*, pp. 40-41 (Oct. 1997).

Buschman, J.P., et al.; "Principles and Problems of Calibration of Fetal Oximeters," *Biomedizinische Technik*, vol. 42, pp. 265-266 (1997).

Pickett, John, et al.; "Pulse Oximetry and PPG Measurements in Plastic Surgery," *Proceedings—19$^{th}$ International Conference—IEEE/EMBS*, Chicago, Illinois, Oct. 30-Nov. 2, 1997, pp. 2330-2332.

Leahy, Martin J., et al.; "Sensor Validation in Biomedical Applications," *IFAC Modelling and Control in Biomedical Systems*, Warwick, UK; pp. 221-226 (1997).

Barreto, Armando B., et al.; "Adaptive LMS Delay Measurement in dual Blood Volume Pulse Signals for Non-Invasive Monitoring," *IEEE*, pp. 117-120 (1997).

Crilly, Paul B., et al.; "An Integrated Pulse Oximeter System for Telemedicine Applications," *IEEE Instrumentation and Measurement Technology Conference*, Ottawa, Canada; May 19-21, 1997; pp. 102-104.

DeKock, Marc; "Pulse Oximetry Probe Adhesive Disks: a Potential for Infant Aspiration," *Anesthesiology*, vol. 89, pp. 1603-1604 (1998).

East, Christine E., et al.; "Fetal Oxygen Saturation and Uterine Contractions During Labor," *American Journal of Perinatology*, vol. 15, No. 6, pp. 345-349 (Jun. 1998).

Rhee, Sokwoo, et al.; "The Ring Sensor: a New Ambulatory Wearable Sensor for Twenty-Four Hour Patient Monitoring," *Proceedings of the 20$^{th}$ annual International Conference of the IEEE Engineering in Medicine and Biology Society*, vol. 20, No. 4, pp. 1906-1909 (Oct. 1998).

Yang, Boo-Ho, et al.; "A Twenty-Four Hour Tele-Nursing System Using a Ring Sensor," *Proceedings of the 1998 IEEE International Conference on Robotics & Automation*, Leaven, Belgium, May 1998; pp. 387-392.

König, Volker, et al.; "Reflectance Pulse Oximetry—Principles and Obstetric Application in the Zurich System," *Journal of Clinical Monitoring and Computing*, vol. 14, pp. 403-412 (1998).

Nogawa, Masamichi, et al.; "A Novel Hybrid Reflectance Pulse Oximater Sensor with improved Linearity and General Applicability to Various Portions of the Body," *Proceedings of the 20$^{th}$ Annual International Conference of the IEEE Engineering in Medicine and Biology Society*, vol. 20, No. 4, pp. 1858-1861 (1998).

Hayes, Matthew J., et al.; "Quantitative evaluation of photoplethysmographic artifact reduction for pulse oximetry," *SPIE*, vol. 3570, pp. 138-147 (Sep. 1998).

Edrich, Thomas, et al.; "Can the Blood Content of the Tissues be Determined Optically During Pulse Oximetry Without Knowledge of the Oxygen Saturation?—An In-Vitro Investigation," *Proceedings of the 20$^{th}$ Annual International conference of the IEEE Engineering in Medicine and Biology Society*, vol. 20, No. 6, pp. 3072-3075 (1998).

Hayes, Matthew J., et al.; "Artifact reduction in photoplethysmography," *Applied Optics*, vol. 37, No. 31, pp. 7437-7446 (Nov. 1998).

Such, Hans Olaf; "Optoelectronic Non-invasive Vascular Diagnostics Using multiple Wavelength and Imaging Approach," *Dissertation*, (1998).

Lutter, N., et al.; "Comparison of Different Evaluation Methods for a Multi-wavelength Pulse Oximeter," *Biomedizinische Technik*, vol. 43, (1998).

Ferrell, T.L., et al.; "Medical Telesensors," *SPIE*, vol. 3253, pp. 193-198 (1998).

Todd, Bryan, et al.; "The Identification of Peaks in Physiological Signals," *Computers and Biomedical Research*, vol. 32, pp. 322-335 (1999).

Rhee, Sokwoo, et al.; "Design of a Artifact-Free Wearable Plethysmographic Sensor," *Proceedings of the First joint BMES/EMBS Conference*, Oct. 13-16, 1999, Altanta, Georgia, p. 786.

Rohling, Roman, et al.; "Clinical Investigation of a New Combined Pulse Oximetry and Carbon Dioxide Tension Sensor in Adult Anaesthesia," *Journal o Clinical Monitoring and Computing*, vol. 15; pp. 23-27 (1999).

Ikeda, Kenji, et al.; "Improvement of Photo-Electric Plethysmograph Applying Newly Developed Opto-Electronic Devices," *IEEE Tencon*, pp. 1109-1112 (1999).

Kaestle, S.; "An Algorithm for Reliable Processing of Pulse Oximetry Signals Under strong Noise Conditions," *Dissertation Book*, Lubeck University, Germany (1999).

Seelbach-Göbel, Birgit, et al.; "The prediction of fetal acidosis by means of intrapartum fetal pulse oximetry," *Am J. Obstet. Gynecol.*, vol. 180, No. 1, Part 1, pp. 73-81 (1999).

Yang, Boo-Ho, et al.; "Development of the ring sensor for healthcare automation," *Robotics and Autonomous Systems*, Vol. 30, pp. 273-281 (2000).

Rhee, Sokwoo, et al.; "Artifact-Resistant, Power-Efficient Design of Finger-Ring Plethysmographic Sensor—Part 1: Design and Analysis," *Proceedings of the 22$^{nd}$ Annual EMBS International Conference*, Chicago, Illinois; Jul. 23-28, 2000; pp. 2792-2795.

Rhee, Sokwoo, et al.; "Artifact-Resistant, Power-Efficient Design of Finger-Ring Plethysmographic Sensor—Part II: Prototyping and Benchmarking," *Proceedings of the 22$^{nd}$ Annual EMBS International Conference*, Chicago, Illinois; Jul. 23-28, 2000; pp. 2796-2799.

Vicenzi, Martin N.; "Transesophageal versus surface pulse oximetry in intensive care unit patients," *Crit. Care Med.*; vol. 28, No. 7, pp. 2268-2270 (2000).

Goldman, Julian M.; "Masimo Signal Extraction Pulse Oximetry," *Journal of Clinical Monitoring and Computing*, vol. 16, pp. 475-483 (2000).

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Nilsson, Lena, et al.; "Monitoring of Respiratory Rate in Postoperative Care Using a New Photoplethysmographic Technique," *Journal of Clinical Monitoring and Computing*, vol. 16, pp. 309-315 (2000).

Nijland, Mark J.M., et al.; "Assessment of fetal scalp oxygen saturation determination in the sheep by transmission pulse oximetry," *Am. J. Obstet Gynecol.*, vol. 183, No. 6, pp. 1549-1553 (Dec. 2000).

Edrich, Thomas, et al.; "Pulse Oximetry: An Improved in Vitro Model that Reduces Blood Flow-Related Artifacts," *IEEE Transactions on Biomedical Engineering*, vol. 47, No. 3, pp. 338-343 (Mar. 2000).

Schulz, Christian Eric; "Design of a Pulse Oximetry Sensor Housing Assembly," California State University Master's Thesis, *UMI Dissertation Services*, UMI No. 1401306, (May 2000) 63 pages.

Yao, Jianchu, et al.; "Design of a Plug-and-Play Pulse Oximeter," *Proceedings of the Second Joint EMBS/BMES Conference*, Houston, Texas, Oct. 23-26, 2002; pp. 1752-1753.

Aoyagi, T., et al.; "Pulse Oximeters: background, present and future," *Neonatal Care*, vol. 13, No. 7, pp. 21-27 (2000) (Article in Japanese—contains English summary of article).

Yokota, Nakaura, Takahashi, et al.; "Pilot Model of a Reflectance-Type Pulse Oximeter for Pre-hospital Evaluation," *Journal of the Japanese Society of Emergency Medicine*, Kanto Region, vol. 21, pp. 26-27 (2000) (Article in Japanese—contains English summary of article).

Kaestle, S.; "Determining Artefact Sensitivity of New Pulse Oximeters in Laboratory Using Signals Obtained from Patient," *Biomedizinische Technik*, vol. 45 (2000).

Cubeddu, Rinaldo, et al.; "Portable 8-channel time-resolved optical imager for functional studies of biological tissues," *Photon Migration, Optical Coherence Tomography, and Microscopy, Proceedings of SPIE*, vol. 4431, pp. 260-265 (2001).

Gisiger, P.A., et al.; "OxiCarbo®, a single sensor for the non-invasive measurement of arterial oxygen saturation and $CO_2$ partial pressure at the ear lobe," *Sensor and Actuators*, vol. B-76, pp. 527-530 (2001).

Cysewska-Sobusaik, Anna; "Metrological Problems With noninvasive Transillumination of Living Tissues," *Proceedings of SPIE*, vol. 4515, pp. 15-24 (2001).

Rhee, Sokwoo, et al.; "Artifact-Resistant, Power-Efficient Design of Finger-Ring Plethysmographic Sensor," *IEEE Transactions on Biomedical Engineering*, vol. 48, No. 7, pp. 795-805 (Jul. 2001).

Belal, Suliman Yousef, et al.; "A fuzzy system for detecting distorted plethysmogram pulses in neonates and paediatric patients," *Physiol. Meas.*, vol. 22, pp. 397-412 (2001).

Hayes, Matthew J., et al.; "A New Method for Pulse Oximetry Possessing Inherent Insensitivity to Artifact," *IEEE Transactions on Biomedical Engineering*, vol. 48, No. 4, pp. 452-461 (Apr. 2001).

Gosney, S., et al.; "An alternative position for the pulse oximeter probe," *Anaesthesia*, vol. 56, p. 493 (2001).

Silva, Sonnia Maria Lopez, et al.; "NIR transmittance pulse oximetry system with laser diodes," *Clinical Diagnostic Systems, Proceedings of SPIE*, vol. 4255, pp. 80-87 (2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Earthrowl-Gould, T., et al.; "Chest and abdominal surface motion measurement for continuous monitoring of respiratory function," *Proc. Instn Mech Engrs*, V215, Part H; pp. 515-520 (2001).

Gehring, Harmut, et al.; "The Effects of Motion Artifact and Low Perfusion on the Performance of a New Generation of Pulse Oximeters in Volunteers Undergoing Hypoxemia," *Respiratory Care*, Vo. 47, No. 1, pp. 48-60 (Jan. 2002).

Jopling, Michae W., et al.; "Issues in the Laboratory Evaluation of Pulse Oximeter Performance," *Anesth Analg*, vol. 94, pp. S62-S68 (2002).

Gostt, R., et al.; "Pulse Oximetry Artifact Recognition Algorithm for Computerized Anaesthetic Records," *Journal of Clinical Monitoring and Computing Abstracts*, p. 471 (2002).

Chan, K.W., et al.; "17.3: Adaptive Reduction of Motion Artifact from Photoplethysmographic Recordings using a Variable Step-Size LMS Filter," *IEEE*, pp. 1343-1346 (2002).

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

Yamaya, Yoshiki, et al.; "Validity of pulse oximetry during maximal exercise in normoxia, hypoxia, and hyperoxia," *J. Appl. Physiol.*, vol. 92, pp. 162-168 (2002).

Lutter, Norbert O., et al.; "False Alarm Rates of Three Third-Generation Pulse Oximeters in PACU, ICU and IABP Patients," *Anesth Analg*, vol. 94, pp. S69-S75 (2002).

Lutter, N., et al.; "Accuracy of Noninvasive Continuous Blood Pressure; Measurement Utilising the Pulse Transit Time," *Journal of clinical Monitoring and Computing*, vol. 17, Nos. 7-8, pp. 469 (2002).

Liu, Ying, et al.; "Sensor design of new type reflectance pulse oximetry," Optics in Health Care and Biomedical Optics: Diagnostics and Treatment, *Proceedings of SPIE*, vol. 4916, pp. 98-102 (2002).

Kyriacou, Panayiotis A., et al.; "Esophageal Pulse Oximetry Utilizing Reflectance Photoplethysmography," *IEEE Transactions on Biomedical Engineering*, vol. 49, No. 11, pp. 1360-1368 (Nov. 2002).

Kyriacou, P. A., et al.; "Investigation of oesophageal photoplethysmographic signals and blood oxygen saturation measurements in cardiothoracic surgery patients," *Physiological Measurement*, vol. 23, No. 3, pp. 533-545 (Aug. 2002).

Tobata, H., et al.; "Study of Ambient Light Affecting Pulse Oximeter Probes," *Ikigaku (Medical Technology)*, vol. 71, No. 10, pp. 475-476 (2002) (Article in Japanese—contains English summary of article).

Irie, A., et al.; "Respiration Monitors—Pulse Oximeters," *Neonatal Care*, vol. 15, No. 12, pp. 78-83 (2002) (Article in Japanese—contains English summary of article).

Koga, I., et al.; "Sigmoid colonic reflectance pulse oximetry and tonometry in a porcine experimental hypoperfusion shock model," *Acta Anaesthesiol Scand*, vol. 46, pp. 1212-1216 (2002).

Shaltis, Phillip, et al.; "Implementation and Validation of a Power-Efficient, High-Speed Modulation Design for Wireless Oxygen Saturation Measurement Systems," *IEEE*, pp. 193-194 (2002).

Warren, Steve, et al.; "Wearable Sensors and Component-Based Design for Home Health Care," *Proceedings of the Second Joint EMBS/BMES Conference*, Houston, Texas; Oct. 23-26, 2002; pp. 1871-1872.

Ericson, M.N., et al.; "In vivo application of a minimally invasive oximetry based perfusion sensor," *Proceedings of the Second Joint EMBS/BMES Conference*, Houston, Texas; Oct. 23-26, 2002; pp. 1789-1790.

Yoon, Gilwon, et al.; Multiple diagnosis based on Photoplethysmography: hematocrib, SpO2, pulse and respiration, Optics in Health Care and Biomedical optics: Diagnostics and Treatment; *Proceedings of the SPIE*, vol. 4916; pp. 185-188 (2002).

Hase, Kentaro, et al.; "Continuous Measurement of Blood Oxygen Pressure Using a Fiber Optic Sensor Based on Phosphorescense Quenching," *Proceedings of the Second Joint EMBS/BMES Conference*, Houston, Texas; Oct. 23-26, 2002, pp. 1777-1778.

Pothisarn, W., et al.; "A non-invasive hemoglobin measurement based pulse oximetry," Optics in Health Care and Biomedical Optics: Diagnostics and Treatment; *Proceedings of SPIE*, vol. 4916; pp. 498-504 (2002).

Tremper, K.K.; "A Second Generation Technique for Evaluating Accuracy and Reliability of Second Generation Pulse Oximeters," *Journal of Clinical Monitoring and Computing*, vol. 16, pp. 473-474 (2002).

Silva, Sonnia Maria Lopez, et al.; "Near-infrared transmittance pulse oximetry with laser diodes," *Journal of Biomedical Optics*, vol. 8, No. 3, pp. 525-533 (Jul. 2003).

Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.

Matthews, Nora S. et al.; "An evaluation of pulse oximeters in dogs, cats and horses," *Veterinary Anaesthesia and Analgesia*, vol. 30, pp. 3-14 (2003).

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Aoyagi, Takuo; "Pulse oximetry: its invention, theory, and future," *Journal of Anesthesia*, vol. 17, pp. 259-266 (2003).

Avidan, A.; "Pulse oximeter ear probe," *Anaesthesia*, vol. 58, pp. 726 (2003).

Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.

Mendelson, Y., et al.; "Measurement Site and Photodetector Size Considerations in Optimizing Power Consumption of a Wearable Reflectance Pulse Oximeter," *Proceedings of the 25th Annual International conference of the IEEE EMBS*, Cancun, Mexico, Sep. 17-21, 2003; pp. 3016-3019.

Itoh, K., et al.; "Pulse Oximeter," *Toyaku Zasshi* (Toyaku Journal), vol. 25, No. 8, pp. 50-54 (2003) (Article in Japanese—contains English summary of article).

Matsui, A., et al.; "Pulse Oximeter," *Neonatal Care*, vol. 16, No. 3, pp. 38-45 (2003) (Article in Japanese—contains English summary of article).

Nakagawa, M., et al.; "Oxygen Saturation Monitor," *Neonatal Monitoring*, vol. 26, No. 5, pp. 536-539 (2003) (Article in Japanese—contains English summary of article).

Kubota, H., et al.; "Simultaneous Monitoring of PtcCO2 and SpO2 using a Miniature earlobe sensor," *Jinko Kokyo (Aritificial Respiration)*, vol. 20, No. 1, pp. 24-29 (2003).

Lebak, J.W., et al.; "Implementation of a Standards-Based Pulse Oximeter on a Wearable, Embedded Platform," *Proceeding of the 25th Annual International Conference of the IEEE EMBS*, Cancun, Mexico, Sep. 17-21, 2003; pp. 3196-3198.

Nagl, L., et al.; "Wearable Sensor System for Wireless State-of-Health Determination in Cattle," *Proceeding of the 25th Annual International Conference of the IEEE EMBS*, Cancun, Mexico, Sep. 17-21, 2003; pp. 3012-3015.

Östmark, Åke, et al.; "Mobile Medical Applications Made Feasible Through Use of EIS Platforms," *IMTC—Instrumentation and Measurement Technology Conference*, Vail, Colorado; May 20-22, 2003; pp. 292-295.

Warren, Steve, et al.; "A Distributed Infrastructure for Veterinary Telemedicine," *Proceedings of the 25th Annual International Conference of the IEEE EMBS*, Cancun, Mexico; Sep. 17-21, 2003; pp. 1394-1397.

Pujary, C., et al.; "Photodetector Size Considerations in the Design of a Noninvasive Reflectance Pulse Oximeter for Telemedicine Applications," *IEEE*, pp. 148-149 (2003).

A. Johansson; "Neural network for photoplethysmographic respiratory rate monitoring," *Medical & Biological Engineering & Computing*, vol. 41, pp. 242-248 (2003).

Reuss, James L.; "Factors Influencing Fetal Pulse Oximetry Performance," *Journal of clinical Monitoring and Computing*, vol. 18, pp. 13-14 (2004).

Mannheimer, Paul D., et al.; "The influence of Larger Subcutaneous Blood Vessels on Pulse Oximetry," *Journal of clinical Monitoring and Computing*, vol. 18, pp. 179-188 (2004).

Wendelken, Suzanne, et al.; "The Feasibility of Using a Forehead Reflectance Pulse Oximeter for Automated Remote Triage," *IEEE*, pp. 180-181 (2004).

Lopez-Silva, S.M., et al.; "Transmittance Photoplethysmography and Pulse Oximetry With Near Infrared Laser Diodes," *IMTC 2004—Instrumentation and Measurement Technology Conference*, Como, Italy, May 18-20, 2004; pp. 718-723.

Sugino, Shigekzau, et al.; "Forehead is as sensitive as finger pulse oximetry during general anesthesia," *Can J Anesth.; General Anesthesia*, vol. 51, No. 5; pp. 432-436 (2004).

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

Jovanov, E., et al.; "Reconfigurable intelligent Sensors for Health Monitoring: A case Study of Pulse Oximeter Sensor," *Proceedings o the $26^{th}$ Annual International conference of the IEEE EMBS*, San Francisco, California, Sep. 1-5, 2004, pp. 4759-4762.

Kocher, Serge, et al.; "Performance of a Digital $PCO_2/SPO_2$ Ear Sensor," *Journal of Clinical Monitoring and Computing*, vol. 18, pp. 75-59 (2004).

Yao, Jianchu, et al.; "A Novel Algorithm to Separate Motion Artifacts from Photoplethysmographic Signals Obtained With a Reflectance Pulse Oximeter," *Proceedings of the $26^{th}$ Annual International conference of the IEEE EMBS*, San Francisco, California, Sep. 1-5, 2004; pp. 2153-2156.

Nuhr, M., et al.: "Forehead $SpO_2$ monitoring compared to finger $SpO_2$ recording in emergency transport," *Anaesthesia*, vol. 59, pp. 390-393 (2004).

Johnston, William S., et al.; "Effects of Motion Artifacts on helmet-Mounted Pulse Oximeter Sensors," 2 pgs. (2004).

Branche, Paul C., et al.; "Measurement Reproducibility and Sensor Placement Considerations in Designing a Wearable Pulse Oximeter for Military Applications," 2 pgs. (2004).

Kocher, Serge, et al.; "Performance of a Digital $PCO_2/SPO_2$ Ear Sensor," *Journal of Clinical Monitoring and Computing*, vol. 18, pp. 75-79 (2004).

Heuss, Ludwig T., et al.; "Combined Pulse Oximetry / Cutaneous Carbon dioxide Tension Monitoring During Colonoscopies: Pilot study with a Smart Ear Clip," *Digestion*, vol. 70, pp. 152-158 (2004).

Matsuzawa, Y., et al.; "Pulse Oximeter," *Home Care Medicine*, pp. 42-45 (Jul. 2004); (Article in Japanese—contains English summary of article).

Crespi, F., et al.; "Near infrared oxymeter prototype for non-invasive analysis of rat brain oxygenation," *Optical Sensing, Proceedings of SPIE*, vol. 5459, pp. 38-45 (2004).

Johnston, W.S., et al.; "Extracting Breathing Rate Infromation from a Wearable Reflectance Pulse Oximeter Sensor," *Proceedings of the $26^{th}$ Annual International conference of the IEEE EMBS*, San Francisco, California; Sep. 1-5, 2004; pp. 5388-5391.

Spigulis, Janis, et al.; "Optical multi-channel sensing of skin blood pulsations," *Optical Sensing, Proceedings of SPIE*, vol. 5459, pp. 46-53 (2004).

Yan, Yong-sheng, et al.; "Reduction of motion artifact in pulse oximetry by smoothed pseudo Wigner-Ville distribution," *Journal of NeuroEngineering and Rehabilitation*, vol. 2, No. 3 (9 pages) (Mar. 2005).

Urquhart, C., et al.; "Ear probe pulse oximeters and neonates," *Anaesthesia*, vol. 60, p. 294 (2005).

Jonnson, P.O. "Patent Cooperation Treaty PCT Written Opinion of the International Searching Authority"; Apr. 20, 2007; 12pp.; European Patent Office; Berlin.

J. Hayoz, et al.; "World's First Combined digital Pulse Oximetry Pulse Oximetry and Carbon Dioxide Tension Ear Sensor", *Abstracts*, A6, p. S103. (undated).

J. Huang, et al.; "Low Power Motion Tolerant Pulse Oximetry," *Abstracts*, A7, p. S103. (undated).

P. Lang, et al.; "Signal Identification and Quality Indicator™ for Motion Resistant Pulse Oximetry," *Abstracts*, A10, p. S105. (undated).

R. Neumann, et al.; "Fourier Artifact suppression Technology Provides Reliable $SpO_2$," *Abstracts*, A 11, p. S105. (undated).

Hamilton, Patrick S., et al.; "Effect of Adaptive Motion-Artifact Reduction on QRS Detection," *Biomedical Instrumentation & Technology*, pp. 197-202 (undated).

Kim, J.M., et al.; "Signal Processing Using Fourier & Wavelet Transform," pp. II-310-II-311 (undated).

Lee, C.M., et al.; "Reduction of Motion Artifacts from Photoplethysmographic Records Using a Wavelet Denoising Approach," *IEEE*, pp. 194-195 (undated).

Nogawa, Masamichi, et al.; "A New Hybrid Reflectance Optical Pulse Oximetry Sensor for Lower Oxygen Saturation Measurement and for Broader Clinical Application," *SPIE*, vol. 2976, pp. 78-87 (undated).

Odagiri, Y.; "Pulse Wave Measuring Device," *Micromechatronics*, vol. 42, No. 3, pp. 6-11 (undated) (Article in Japanese—contains English summary of article).

Yamazaki, Nakaji, et al.; "Motion Artifact Resistant Pulse Oximeter (Durapulse PA 2100)," *Journal of Oral Cavity Medicine*, vol. 69, No. 4, pp. 53 (date unknown) (Article in Japanese—contains English summary of article).

\* cited by examiner

MEANS FOR MECHANICAL REGISTRATION AND MECHANICAL-ELECTRICAL COUPLING OF A FARADAY SHIELD TO A PHOTODETECTOR AND AN ELECTRICAL CIRCUIT

BACKGROUND OF THE INVENTION

1. Field of the Invention

The present invention relates generally to medical devices and, more particularly, to sensors used for sensing physiological parameters of a patient.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, and/or the rate of blood pulsations corresponding to each heartbeat of a patient.

Pulse oximeters typically utilize a non-invasive sensor that is placed on or against a patient's tissue that is well perfused with blood, such as a patient's finger, toe, forehead or earlobe. During operation of a pulse oximeter, an emitter emits light, and a photodetector, photoelectrically senses the absorption and/or scattering of the light after passage through the perfused tissue. The data collected by the sensor may then be used to calculate one or more of the above physiological characteristics based upon the absorption or scattering of the light. More specifically, the emitted light is typically selected to be of one or more wavelengths that are absorbed or scattered in an amount related to the presence of oxygenated versus de-oxygenated hemoglobin in the blood. The amount of light absorbed and/or scattered may then be used to estimate the amount of the oxygen in the tissue using various algorithms.

In many instances, pulse oximeter sensors are susceptible to electrical noise interference from outside sources. For example, electrical components of pulse oximeter sensors may be susceptible to electromagnetic interference (EMI). Electromagnetic interference occurs when the electromagnetic fields from one device interfere with the operation of some other device. For example, devices nearby or contained within the pulse oximeter sensor may emit electromagnetic fields that interfere with the pulse oximeter's operation. Also, electrical noise may be coupled to the sensor directly from the patient through the skin. Electromagnetic interference can cause reduced data integrity and increased error rates of sensors. Accordingly, a pulse oximeter sensor may experience inaccurate results if it is exposed to and not protected from electromagnetic signals. Therefore, it is desirable to employ protection of pulse oximeter sensors from EMI.

In the case of pulse oximeter sensors, protection from EMI may be provided by encompassing the photodetector of the sensor in a "cage" or "box" of conductive material (often referred to as a "Faraday shield" or "Faraday cage") and electrically coupling the cage to the ground plane of the circuitry in the pulse oximeter sensor. Grounding of the cage completes the ground loop, providing shielding of the sensor components from the EMI fields. By shielding the photodetector of the pulse oximeter sensor, errors from induced electrical noise are mitigated. However, placing and securing the Faraday shield accurately about the photodetector may be a delicate and manually labor intensive procedure, as care may be required during assembly to not have any part of the Faraday material encroach onto the photodetector's field of view.

SUMMARY

Certain aspects commensurate in scope with the originally claimed invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

In accordance with one aspect of the present invention, there is provided a Faraday shield assembly, comprising: a Faraday shield structure configured for use within a biometric sensor; and at least one alignment feature; configured to provide mechanical registration of the Faraday shield structure in reference to a photometric device.

In accordance with another aspect of the present invention, there is provided a spectrophotometric sensor assembly, comprising: mating surface of a biometric sensor circuitry; a photodetector disposed on the mating surface; and a Faraday shield assembly comprising: a Faraday shield structure disposed about the photodetector; and at least one alignment feature; configured to facilitate mechanical registration of the Faraday shield structure to the mating surface.

In accordance with another aspect of the present invention, there is provided a method of manufacturing a spectrophotometric sensor, the method comprising: providing a photodetector on a mating surface of spectrophotometric sensor circuitry; and securing a Faraday shield assembly to the mating surface such that a Faraday shield structure of the Faraday shield assembly is disposed about the photodetector and the Faraday shield is mechanically registered to the mating surface based on an alignment feature of the Faraday shield assembly.

BRIEF DESCRIPTION OF THE DRAWINGS

Advantages of the invention may become apparent upon reading the following detailed description and upon reference to the drawings in which:

FIG. 4 illustrates a perspective view of the Faraday shield assembly of FIG. 2 encompassing a photodetector on a mating surface with a conductive substance electrically coupling the Faraday shield assembly to the mating surface, in accordance with aspects of the present technique; and.

DETAILED DESCRIPTION OF SPECIFIC EMBODIMENTS

Figure 1:
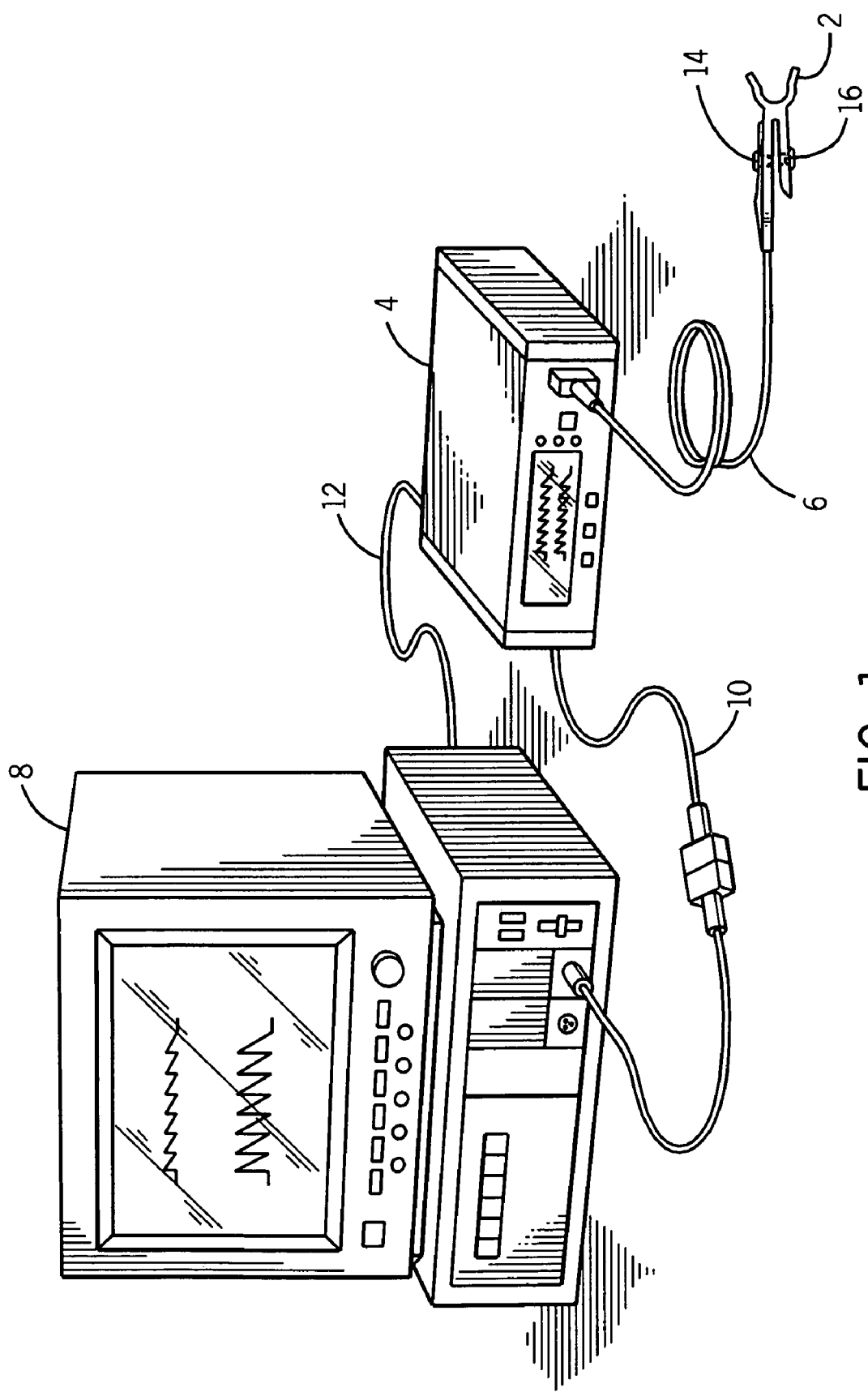
FIG. 1 illustrates a patient monitoring system coupled to a multi-parameter patient monitor and a sensor, in accordance with aspects of the present technique.

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

It is desirable to provide an accurate and reliable sensor, such as for use in pulse oximetry or other applications utilizing spectrophotometry, that is easily assembled and that is resistant to electromagnetic interference (EMI). In accordance with some aspects of the present technique, a patient sensor assembly is provided that includes a Faraday shield that simplifies registration of the Faraday shield to the sensor's field of view, and provides for electrical coupling of the Faraday shield to an electrical circuit's ground plane. Alignment features present on the Faraday shield provide for registration of the Faraday shield with a photodetector contained in the sensor assembly, and the alignment features may also provide for electrical coupling to an electrical circuit's ground plane to reduce EMI. Not only does the present technique facilitate manual construction of the sensor, but it may also facilitate the Faraday shield to be placed in an automated or semi-automated fashion while achieving proper alignment of the Faraday shield and EMI protection, both contributing to optimize performance and minimize errors in the sensor's results.

Prior to discussing such exemplary sensors and Faraday shields in detail, it should be appreciated that such sensors are typically designed for use with a patient monitoring system. For example, referring now to FIG. 1, a sensor 2 according to the present invention may be used in conjunction with a patient monitor 4. In the depicted embodiment, a cable 6 connects the sensor 2 to the patient monitor 4. As will be appreciated by those of ordinary skill in the art, the sensor 2 and/or the cable 6 may include or incorporate one or more integrated circuit devices or electrical devices, such as a memory, processor chip, or resistor, that may facilitate or enhance communication between the sensor 2 and the patient monitor 4. Likewise the cable 6 may be an adaptor cable, with or without an integrated circuit or electrical device, for facilitating communication between the sensor 2 and various types of monitors, including older or newer versions of the patient monitor 4 or other physiological monitors. In other embodiments, the sensor 2 and the patient monitor 4 may communicate via wireless means, such as using radio, infrared, or optical signals. In such embodiments, a transmission device (not shown) may be connected to the sensor 2 to facilitate wireless transmission between the sensor 2 and the patient monitor 4. As will be appreciated by those of ordinary skill in the art, the cable 6 (or corresponding wireless transmissions) is typically used to transmit control and/or timing signals from the patient monitor 4 to the sensor 2 and/or to transmit acquired data from the sensor 2 to the patient monitor 4. In some embodiments, however, the cable 6 may be an optical fiber that allows optical signals to be conducted between the patient monitor 4 and the sensor 2.

In one embodiment, the patient monitor 4 may be a suitable pulse oximeter, such as those available from Nellcor Puritan Bennett Inc. In other embodiments, the patient monitor 4 may be a monitor suitable for measuring tissue water fractions, or other body fluid related metrics, using spectrophotometric or other techniques. Also, the patient monitor 4 may be a multi-purpose monitor suitable for performing pulse oximetry and measurement of tissue water fraction, or other combinations of physiological and/or biochemical monitoring processes, using data acquired via the sensor 2. Furthermore, for the patient monitor 4 to provide additional functions, the patient monitor 4 may be coupled to a multi-parameter patient monitor 8 via a cable 10 connected to a sensor input port and/or via a cable 12 connected to a digital communication port.

The sensor 2, in the example depicted in FIG. 1, is a clip-style sensor that is overmolded to provide a unitary or enclosed assembly. The sensor 2 includes an emitter 14 and a detector 16 which may be of any suitable type. For example, the emitter 14 may be one or more light emitting diodes adapted to transmit one or more wavelengths of light, such as in the red to infrared range, and the detector 16 may be a photodetector, such as a silicon photodiode package, selected to receive light in the range emitted from the emitter 14. In the depicted embodiment, the sensor 2 is coupled to a cable 6 that is responsible for transmitting electrical and/or optical signals to and from the emitter 14 and detector 16 of the sensor 2. The cable 6 may be permanently coupled to the sensor 2, or it may be removably coupled to the sensor 2—the latter alternative being more useful and cost efficient in situations where the sensor 2 is disposable.

The sensor 2 discussed herein may be configured for either transmission or reflectance type sensing. Furthermore, the sensor 2 may include various structural and functional features designed to facilitate its use. An example of such a sensor and its use and construction may be found in U.S. application Ser. No. 11/199,524 titled "Medical Sensor and Technique for Using the Same" and filed on Aug. 8, 2005, which is hereby incorporated by reference in its entirety. As will be appreciated by those of ordinary skill in the art, however, such discussion is merely exemplary and is not intended to limit the scope of the present technique.

Figure 2:
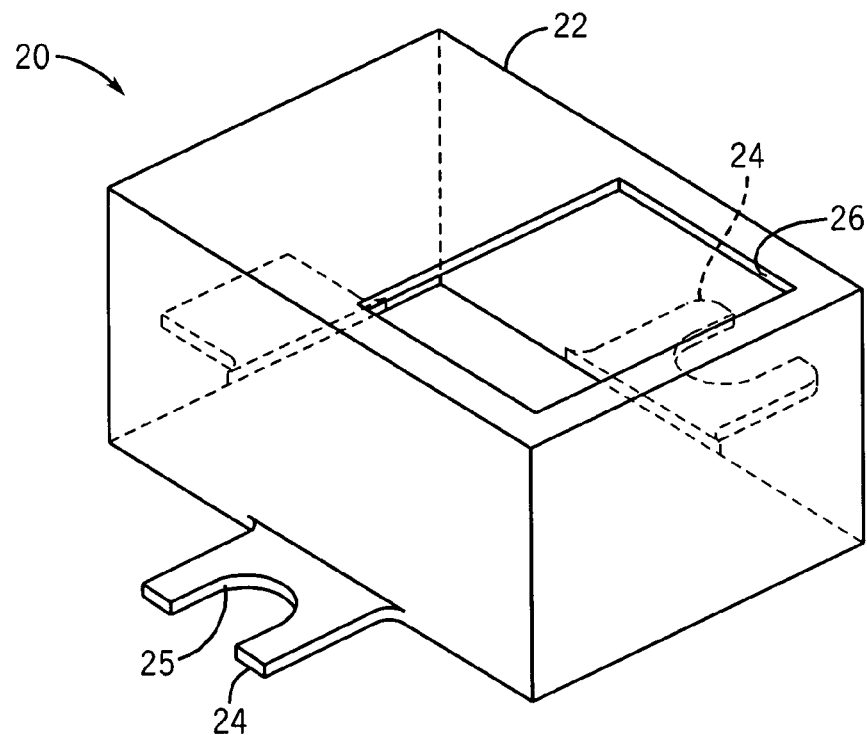
FIG. 2 illustrates a perspective view of a Faraday shield assembly for use in a patient sensor, in accordance with aspects of the present technique.

Referring now to FIG. 2, a perspective view of a Faraday shield assembly 20 for use in a sensor 2 is depicted. Such a Faraday shield assembly 20 may include various structures and features. For example, the depicted Faraday shield assembly includes a Faraday shield structure 22 that is generally box-like. As will be appreciated by those of ordinary skill in the art, in view of serving its function as a Faraday shield, the Faraday shield structure 22 is not limited to a box-like shape, but may take a multitude of shapes and dimensions to achieve the function of providing Faraday shielding.

Figure 3:
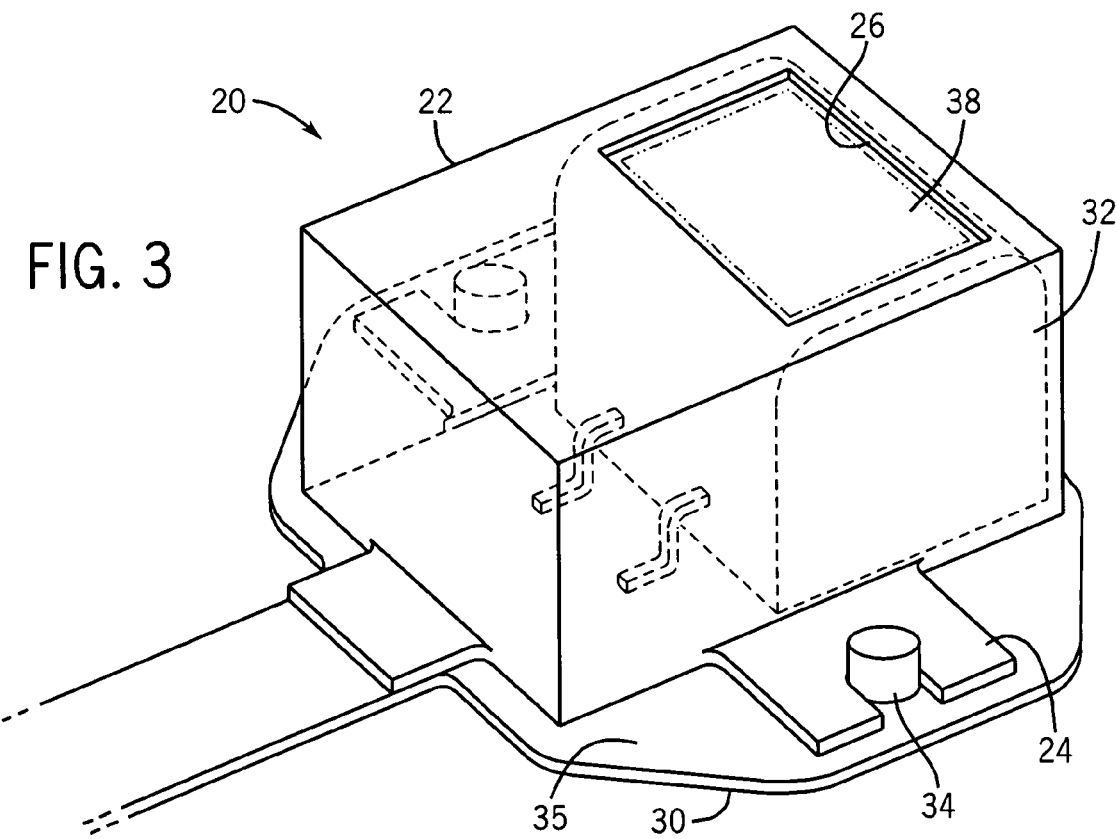
FIG. 3 illustrates a perspective view of the Faraday shield assembly of FIG. 2 encompassing a photodetector on a mating surface, in accordance with aspects of the present technique.

In addition, the Faraday shield assembly 20 may include one or more alignment features 24. The alignment feature(s) 24, may facilitate mechanical registration of the Faraday shield assembly 20 to a mating surface 30 of the electrical circuit, as depicted in FIG. 3. For example, the depicted alignment feature 24, includes a notch 25 which is capable of accepting a corresponding or complementary mating pin (as depicted in FIG. 3 by a mating alignment feature 34) on a mating surface 30. As will be appreciated by those of ordinary skill in the art, the alignment feature 24 may take any form which aides in alignment or registration of the Faraday shield assembly 20. For example, the alignment feature 24 may include features to aide in visual alignment (i.e., markings) or may take the form of mechanical alignment features such as depressions and/or raised the surfaces (i.e., protrusions, tabs, slots, and so forth), as well as any combination of numbers and forms of alignment features.

In one embodiment the sensor 2 may include a photodetector 32, as depicted in FIG. 3. In these or similar embodiments, it may be beneficial for the Faraday shield structure 22 to include an aperture to allow an increased amount of light to reach the photodetector 32. For example, the depicted Faraday shield assembly 20 includes an aperture 26. The aperture 26 allows an appropriate amount of light to reach the photodetector 32 in the region actively used for detection, i.e., the photodetector's field of view.

Figure 5:
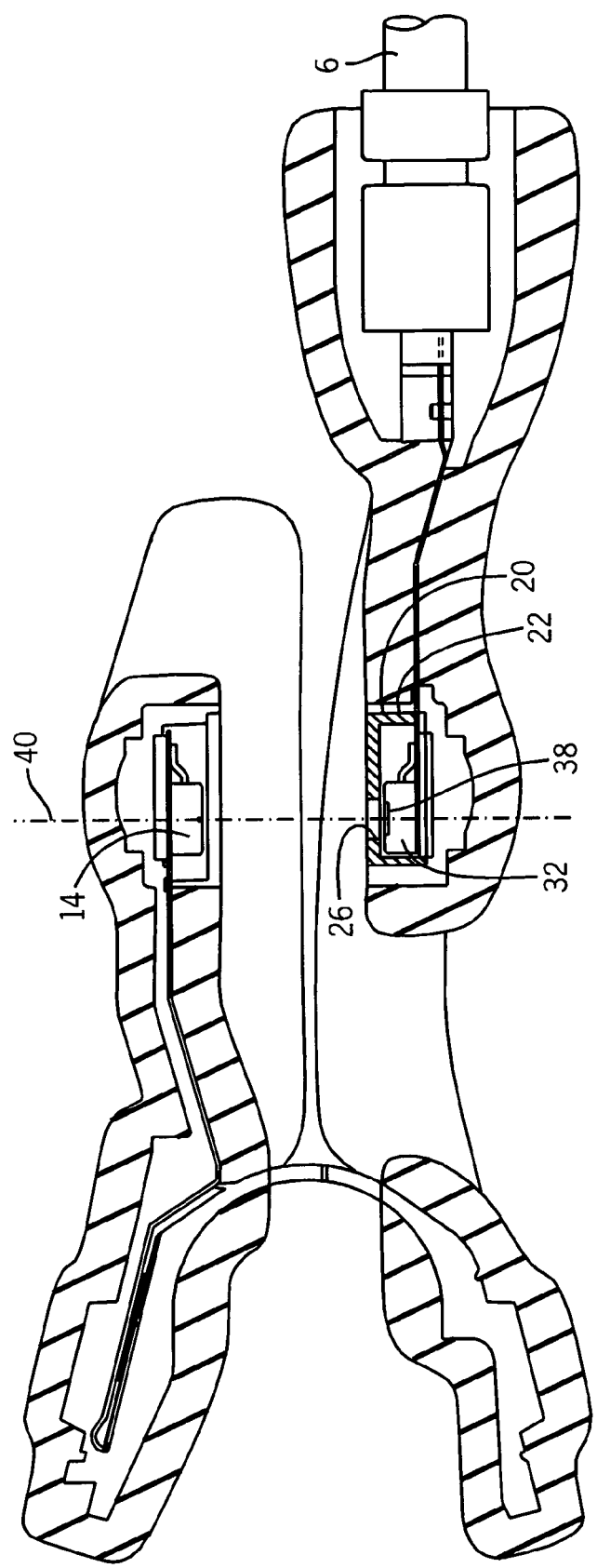
FIG. 5 illustrates a cross sectional view of a pulse oximeter comprising a Faraday shield assembly, in accordance with aspects of the present technique

In an embodiment noted above, the alignment feature 24 of the Faraday shield assembly 20 may be useful in aligning and registering the Faraday shield assembly 20 to the mating surface 30. Likewise, the alignment features 24 may also provide registration of an aperture 26 to the field of view 38 of a corresponding photodetector 32. For instance, as depicted in FIG. 3, the alignment feature 24 of the Faraday shield assembly 20 may be employed to provide registration of aperture 26 relative to the field of view 38. In another embodiment, where the emitter 14 and photodetector 32 are aligned for transmission style of sensing, it may be desirable for the field of view 38 of the photodetector 32 and the aperture 26 of the Faraday shield assembly, to align with the emitter 14. For example, FIG. 5 depicts the sensor field of view 38, the aperture 26, and the emitter 14 aligned about optical axis 40.

In consideration of the embodiments already discussed, one of ordinary skill in the art will appreciate that alignment features 24 integrated in a Faraday shield assembly 20 may provide mechanical registration of both the Faraday shield structure 22, as well as features of the Farday shield assembly 20, including an aperture 26. This alignment feature 24 facilitates the alignment and assembly of the Faraday shield assembly 20 about the photodetector 32. For example, with alignment features 24 as disclosed, a pulse oximeter, including a Farday shield assembly 20, may be automatically or semi-automatically manufactured (as opposed to manual alignment and placement) while still achieving accurate placement of the Faraday shield assembly 20 about the photodetector 32. For example, a pick and place machine may be used to automatically place the Faraday shield assembly 20 during the manufacture of the sensor 2.

Figure 4:
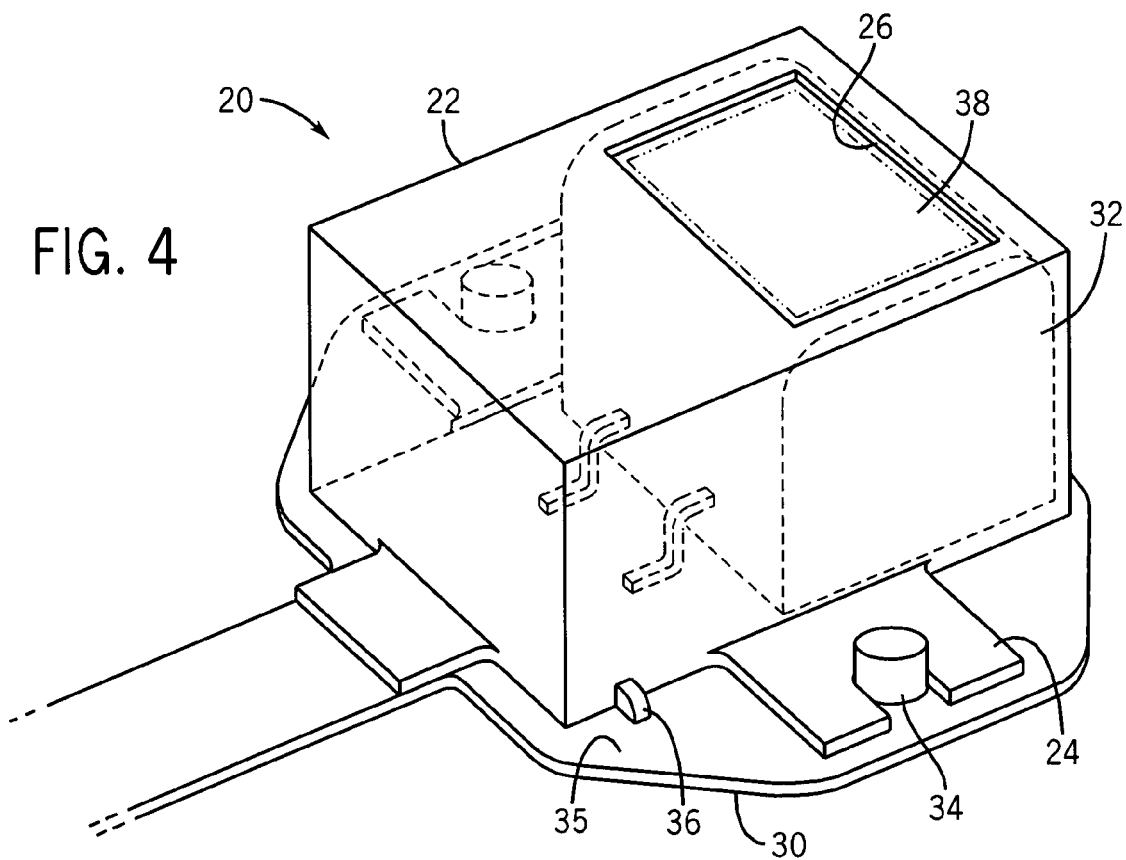

In addition to providing mechanical registration of the Faraday shield assembly 20, in another embodiment, the alignment feature 24 may provide electrical coupling of the Faraday shield assembly 20 to a ground plane 35 of the mating surface 30. For example, in the embodiment depicted in FIG. 3, the alignment feature 24 may contact the ground plane 35 of the mating surface 30. In another embodiment, the alignment feature 24 may contact a mating alignment feature 34 that is conductively coupled to the ground plane 35 of the mating surface 30 and thereby provides electrical coupling of the Faraday shield assembly 20 to the ground plane 35. In another embodiment, the Faraday shield assembly 20 may not be electrically coupled to the ground plane 35 solely via the alignment feature 24. Instead, the Faraday shield assembly 20 may be electrically coupled to the ground plane 35 via another path. For example, as depicted in FIG. 4, a conductive substance 36 may electrically couple the Faraday shield assembly 20 and the ground plane 35. As will be appreciated by those of ordinary skill in the art, the conductive substance 36 may include but is not limited to substances such as a metallic solder material.

In other embodiments, the material used to form the Faraday shield structure 22 and/or the Faraday shield assembly 20 may be varied. As will be appreciated by those of ordinary skill in the art, the material used to create such a Faraday shield structure 22 includes, but is not limited to copper. In addition to copper, the Faraday shield structure 22 may be formed from other conductive materials. In further embodiments, the form of the material used, to create the Faraday shield structure 22 may vary. For example, the Faraday shield structure 22 may be formed of a solid conductive material, or the Faraday shield structure 22 may be formed of a conductive mesh. Further, the thickness of the Faraday shield structure 22 may vary. For example, the thickness of the Faraday shield structure 22 may vary from a thin foil to a material of substantial thickness.

While the exemplary medical sensors 2 discussed herein are some examples of medical devices employing a Faraday shield, other such devices are also contemplated and fall within the scope of the present disclosure. For example, other medical sensors and/or contacts applied externally to a patient may be advantageously applied using Faraday shield assembly as discussed herein. For example, other spectrophotometric applications where a probe is attached to a patient may utilize a sensor as described herein.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims. Indeed, the present techniques may not only be applied to transmission type sensors for use in pulse oximetry, but also to retroflective and other sensor designs as well.

What is claimed is:

1. A Faraday shield assembly, comprising:
   a Faraday shield structure configured to be mounted within a biometric sensor; and
   at least one alignment feature that provides mechanical registration of the Faraday shield structure in reference to a photometric device, wherein the alignment feature is electrically couples to a corresponding alignment feature or to circuitry of the biometric sensor.

2. The Faraday shield assembly of claim 1, wherein a conductive substance electrically couples the Faraday shield structure to circuitry of the biometric sensor.

3. The Faraday shield assembly of claim 1, wherein the Faraday shield structure is comprised of a conductive mesh material.

4. The Faraday shield assembly of claim 1, wherein the Faraday shield structure is comprised of a solid conductive material.

5. The Faraday shield assembly of claim 1, wherein the Faraday shield structure comprises an aperture configured to facilitate a sensor field of view.

6. A spectrophotometric sensor assembly, comprising:
   a mating surface of a biometric sensor circuitry;
   a photodetector disposed on the mating surface; and
   a Faraday shield assembly comprising:

a Faraday shield structure disposed about the photodetector; and at least one alignment feature configured to facilitate mechanical registration of the Faraday shield structure to the mating surface.

7. The spectrophotometric sensor assembly of claim 6, wherein the alignment feature is electrically coupled to the biometric sensor circuitry.

8. The spectrophotometric sensor assembly of claim 6, wherein a conductive substance electrically couples the Faraday shield to the biometric sensor circuitry.

9. The spectrophotometric sensor assembly of claim 6, wherein the alignment feature mechanically fastens the Faraday shield assembly to the mating surface.

10. The spectrophotometric sensor assembly of claim 6, wherein the Faraday shield structure comprises an aperture corresponding to a field of view of the photodetector.

11. The spectrophotometric sensor assembly of claim 10, wherein the alignment feature provides registration of the aperture and the field of view of the photodetector.

12. The spectrophotometric sensor assembly of claim 6, wherein the photodetector comprises a photodiode.

13. The spectrophotometric sensor assembly of claim 6, comprising a pulse oximetry sensor, a sensor for measuring a water fraction, or a combination thereof.

14. The spectrophotometric sensor assembly of claim 6, wherein the Faraday shield structure is comprised of a conductive mesh material.

15. The spectrophotometric sensor assembly of claim 6, wherein the Faraday shield structure is comprised of a solid conductive material.

16. A method of manufacturing a spectrophotometric sensor, the method comprising:

providing a photodetector on a mating surface of spectrophotometric sensor circuitry; and securing a Faraday shield assembly to the mating surface such that a Faraday shield structure of the Faraday shield assembly is disposed about the photodetector and the Faraday shield is mechanically registered to the mating surface based on an alignment feature of the Faraday shield assembly.

17. The method of claim 16, comprising affixing the alignment feature to the mating surface to provide electrical coupling of the Faraday shield assembly to the spectrophotometric sensor circuitry.

18. The method of claim 16, comprising providing a conductive substance to electrically couple the Faraday shield assembly to the spectrophotometric sensor circuitry.

19. The method of claim 16, wherein securing the Faraday shield assembly to the mating surface comprises mechanically affixing the alignment feature to the mating surface.

20. The method of claim 16, wherein securing the Faraday shield assembly to the mating surface is performed automatically or semi-automatically.

21. The method of claim 16, comprising registering an aperture on the Faraday shield assembly with a field of view of the photodetector.

* * * * *